US011197674B2

(12) United States Patent
Krupp et al.

(10) Patent No.: US 11,197,674 B2
(45) Date of Patent: Dec. 14, 2021

(54) HAIR GRASPING DEVICE

(71) Applicant: TLA M.D., LLC, North Liberty, IA (US)

(72) Inventors: David Carl Krupp, North Liberty, IA (US); Kathleen Bartel, Rockford, IL (US); Maddie Dietz, Los Angeles, CA (US); Alyssa Esquivel, Kansas City, MO (US); Tracy Piplani, St. Paul, MN (US); Charles E. Romans, North Liberty, IA (US)

(73) Assignee: 11:11, LLC, North Liberty, IA (US)

(*) Notice: Subject to any disclaimer, the term of this patent is extended or adjusted under 35 U.S.C. 154(b) by 306 days.

(21) Appl. No.: 15/949,957

(22) Filed: Apr. 10, 2018

(65) Prior Publication Data

US 2018/0289373 A1    Oct. 11, 2018

Related U.S. Application Data

(60) Provisional application No. 62/483,627, filed on Apr. 10, 2017.

(51) Int. Cl.
*A61B 17/08* (2006.01)
*A61B 17/28* (2006.01)
*A61B 17/00* (2006.01)

(52) U.S. Cl.
CPC .............. *A61B 17/08* (2013.01); *A61B 17/28* (2013.01); *A61B 17/00491* (2013.01);
(Continued)

(58) Field of Classification Search
CPC ........... A61B 2017/00752; A61B 2018/00476; A61B 17/28; A61B 17/08–083;
(Continued)

(56) References Cited

U.S. PATENT DOCUMENTS 2,584,547 A * 2/1952 Cahn .................. A45D 26/0071
606/133
3,541,591 A    11/1970 Hoegerman
(Continued)

FOREIGN PATENT DOCUMENTS

EP    1164887    1/2004
GB    449001    6/1936
(Continued)

OTHER PUBLICATIONS

PCTUS1826950 Written Opinion of the International Searching Authority—dated Aug. 24, 2019.
Dec. 2, 2020 Search Report—PCTUS2018026950.

*Primary Examiner* — Darwin P Erezo
*Assistant Examiner* — Brigid K Byrd
(74) *Attorney, Agent, or Firm* — Nyemaster Goode, PC

(57) ABSTRACT

A hair grasping device comprising a handle and a grasping mechanism on an end of the handle. The grasping mechanism includes a finger having a handle end and a grasping end and a hair grip extending from the grasping end of the finger. The hair grip and the finger are moveable with respect to one another between a hair grasping position and a hair holding position and the hair grip is operably coupled with the finger when in the hair holding position.

13 Claims, 25 Drawing Sheets

(52) U.S. Cl.
CPC ............... *A61B 2017/00349* (2013.01); *A61B 2017/081* (2013.01); *A61B 2017/088* (2013.01)

(58) Field of Classification Search
CPC ...... A61B 2017/088; A61B 2017/2906; A61B 17/295; A61B 2017/00349; A45D 26/0023; A45D 26/0042; A45D 26/0066
See application file for complete search history.

(56) References Cited

U.S. PATENT DOCUMENTS

| | | | |
|---|---|---|---|
| 3,735,765 A | | 5/1973 | Ichelson |
| 4,174,713 A | * | 11/1979 | Mehl ..................... A61B 18/14 606/42 |
| 4,378,019 A | * | 3/1983 | Yamada .................... A61F 2/10 606/187 |
| 4,744,145 A | * | 5/1988 | Lee ......................... B26B 13/18 30/134 |
| 4,994,061 A | * | 2/1991 | McPherson ............ A61B 18/14 606/133 |
| 5,176,703 A | | 1/1993 | Peterson |
| 5,281,237 A | | 1/1994 | Gimpelson |
| 5,474,057 A | * | 12/1995 | Makower ........... A61B 17/0218 600/214 |
| 5,613,937 A | | 3/1997 | Garrison et al. |
| 5,618,307 A | | 4/1997 | Donlon et al. |
| 6,973,931 B1 | | 12/2005 | King |
| 8,322,353 B2 | | 12/2012 | Russell |
| 8,770,207 B2 | | 7/2014 | Yoshimasa |
| 8,920,442 B2 | | 12/2014 | Sibbitt et al. |
| 2010/0185213 A1 | | 7/2010 | Lam |
| 2017/0013928 A1 | | 1/2017 | Debenedictis et al. |
| 2018/0256181 A1 | * | 9/2018 | Bonadio ................ A61B 90/08 |

FOREIGN PATENT DOCUMENTS

| | | |
|---|---|---|
| GB | 962626 | 7/1964 |
| WO | 2007112072 | 10/2007 |

* cited by examiner

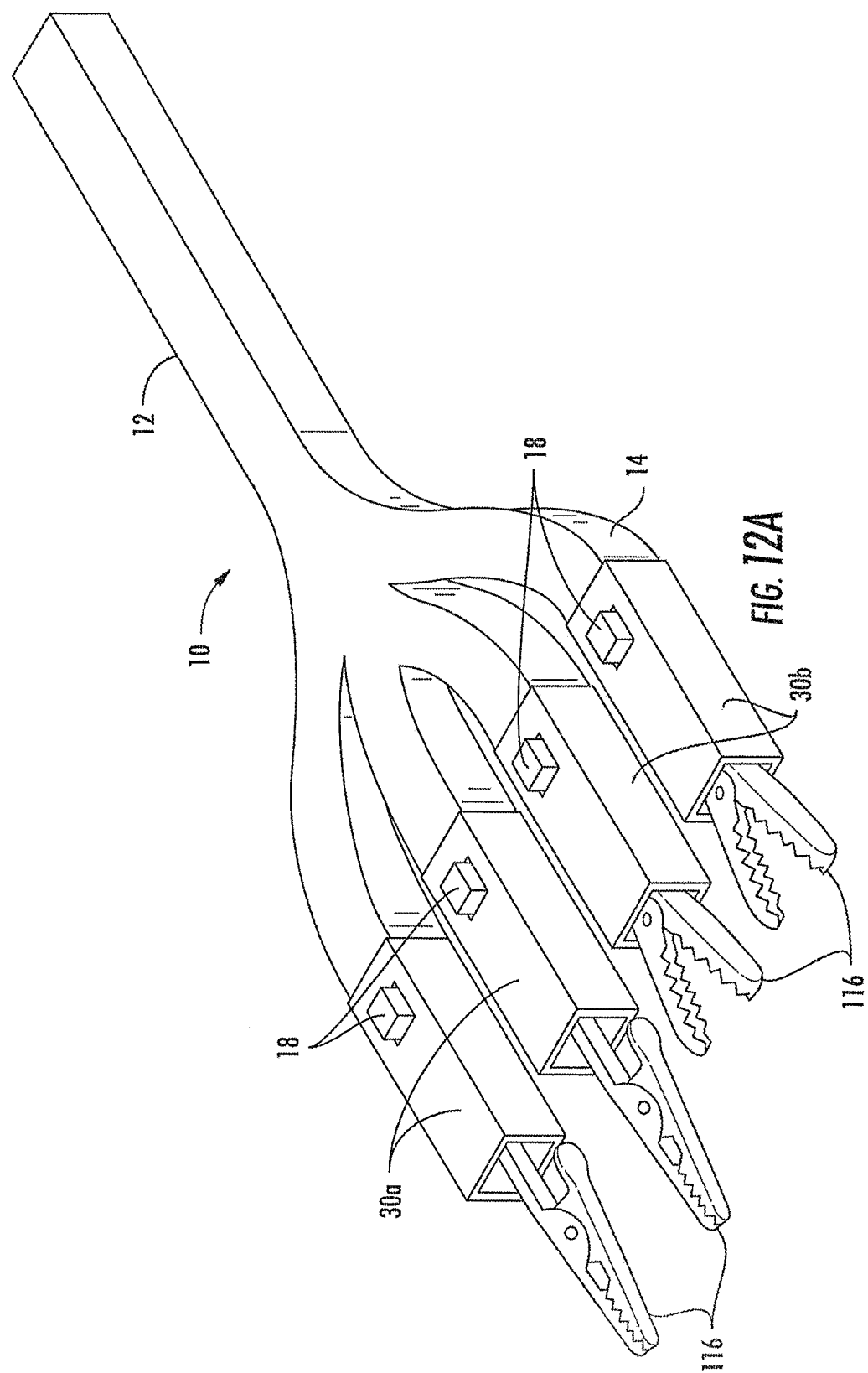

HAIR GRASPING DEVICE

This application is based upon U.S. Provisional Application Ser. No. 62/483,627 filed Apr. 10, 2017, the complete disclosure of which is hereby expressly incorporated by this reference.

BACKGROUND OF THE DISCLOSURE

An estimated 7.3 million lacerations are seen in emergency departments and other clinics in the United States every year. Approximately 800,000 of these are scalp lacerations. Currently, the most common methods for closing scalp lacerations are sutures and staples. However, both these approaches require local anesthetics, are painful for the patient, and often require a follow-up visit for their removal. A less common technique for closing scalp lacerations is the hair apposition technique (HAT). The HAT is non-invasive, requires no anesthetics, and usually does not require a follow-up visit. The HAT utilizes the patient's own hair to help close the wound. Although the HAT overcomes some of the drawbacks of sutures and staples, the HAT can be difficult and time consuming for medical professionals since it can be hard to grasp and pull clusters of hair across the wound. There is therefore a need for a device which grabs and pulls hair across a wound to simplify the HAT.

SUMMARY OF THE PRESENT DISCLOSURE

One aspect of the present disclosure includes a hair grasping device having a handle and a grasping mechanism on an end of the handle. The grasping mechanism has at least one finger with a handle end and a grasping end. The grasping end of the finger includes a hair grip extending therefrom. In some embodiments, the hair grip and the finger are moveable with respect to one another between a hair grasping position and a hair holding position so that the hair grip is operably coupled with the finger when in the hair holding position to help secure the hair between the hair grip and the finger. The device also has a trigger operably coupled with the grasping mechanism to move the grasping mechanism between the hair grasping position and the hair holding position. The hair grip may be any member capable of grabbing and pulling a cluster of hair, including hooks, pincers, vacuum, tape, hook and loop fasteners, screws, and chemical attachments.

Another aspect of the present disclosure includes a hair grasping device having a handle and a grasping mechanism on an end of the handle. The grasping mechanism includes at least one finger having an channel or opening therein between a handle end and a grasping end. The grasping mechanism further includes a hair grip such as a hook having a base, a tip, and a bend, wherein the hook extends from the grasping end of the finger. The hook and the finger are moveable with respect to one another between a hair grasping position and a hair holding position. The hook is operably coupled with the finger when in the hair holding position to help secure the hair between the hook and the finger. The device also has a slide with a trigger in the grip and operably coupled with the grasping mechanism.

Another aspect of the present disclosure includes a hair grasping device having a handle with an opening therein, a grip portion, at least two fingers each having a handle end and a grasping end, wherein the at least two fingers are spaced apart by at least the width of one of the at least two fingers. There are at least two hair grips within the at least two fingers, at least a portion of the at least two grips extending from the grasping end of each of the at least two fingers. There is a trigger in the handle and connected to the at least two grips for moving the hair grips between a hair grasping position and a hair holding position.

Yet another aspect of the present disclosure includes a hair grasping device having a handle, a finger with an opening therein attached to an end of the handle, the finger further having a grasping end, and a hook having a base, a tip, and a bend, wherein the hook extends from the grasping end of the finger. One of the hook and the hollow finger are slidably moveable along an axis of the finger between a hair grasping position and a hair holding position and the hook is operably coupled with the finger when in the hair holding position. The device also has a trigger attached to one of the hook and the hollow finger.

Yet another aspect of the present disclosure relates to a method of using one of the hair grasping devices disclosed above. The method includes using a tool to isolate small groupings of hair on one side of a wound. The device is moved to the hair grasping position and the groupings of hair are grasped by the hair grip. The device is then moved to the hair holding position wherein the groupings of hair are secured by the device. The groupings of hair are pulled across the wound. The wound may then be closed using a tissue adhesive (glue) or by tying the hair to other hair on the distal side of the wound. In some embodiments, two hair grasping devices may be used as the same time to grasp hair on opposite sides of the wound and correspondingly pull the hair to the other side of the wound. The hairs would be crossed synchronously with tension applied to close the wound. These crossed sections of hair would then be secured with a tissue adhesive or any other suitable means.

BRIEF DESCRIPTION OF THE DRAWINGS

In the drawings:

FIG. 12A is an isometric view of another embodiment of the hair grasping device.

DETAILED DESCRIPTION OF EMBODIMENTS

Figure 1:
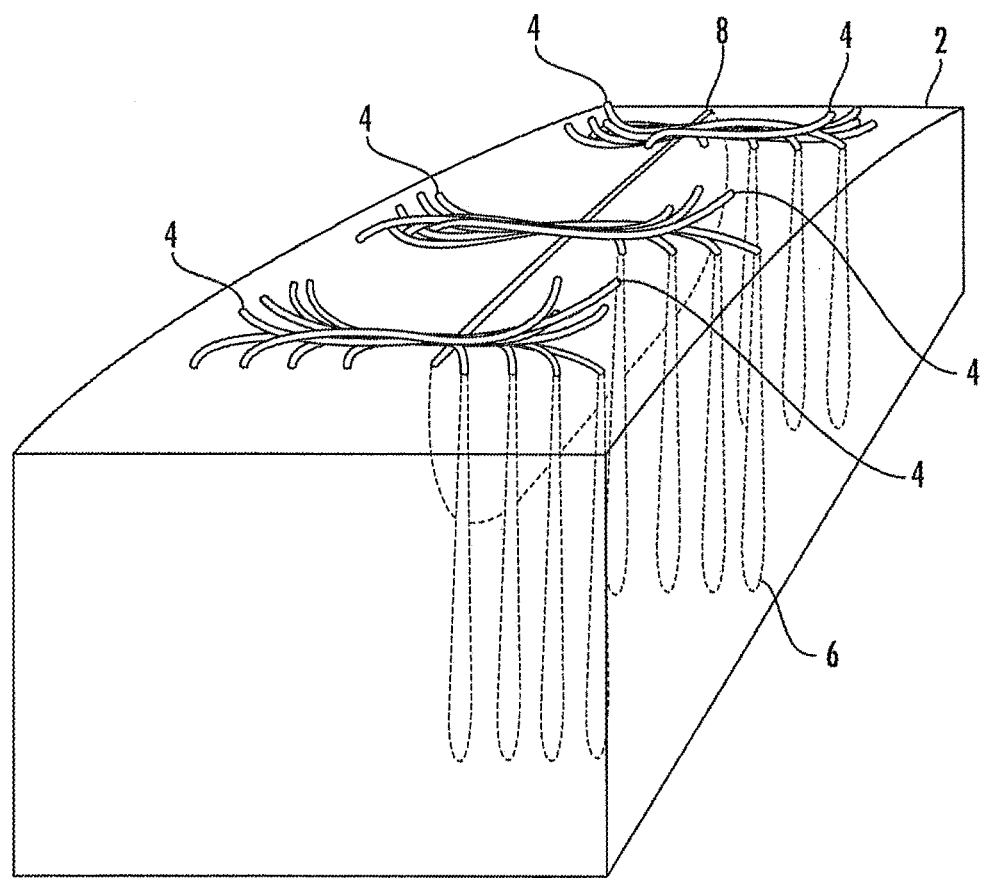
FIG. 1 is a diagram showing a wound closed using the hair apposition technique.

Described herein are various configurations and designs for a device that grabs hair 4 and holds it in tension, such as a hand held tool for, in some instances, closing lacerations. The following description and drawings sufficiently illustrate specific examples to enable those skilled in the art to practice them. Other examples may incorporate structural and other changes. Portions and features of some examples may be included in, or substituted for, those of other examples. As used within this description, corresponding portions of differing embodiments will be shown using similar reference numerals with a different numeral in the hundreds place.

FIG. 1 shows the end result of a wound such as a laceration 8 which has been closed using the device described herein. A person or animal may incur some injury that causes a laceration 8 on a patch of skin 2 that is surrounded by some hair 4. An example of this is on the scalp of a person's head. Instead of using a sutures, staples, stitches, or some other means for closing the laceration 8, the person's own hair 4 is used to pull the skin on either side of the laceration 8 together. The hair 4 is grabbed and pulled across the laceration 8 by the device 10 and then closed using an adhesive glue 5, tying the hair 4 together, or held together in some other fashion to hold the laceration 8 closed.

Turning now to FIGS. 2A-8, a hair grasping device 10 is shown having a handle 12, a plurality of spaced apart fingers 14, a plurality of hair grips such as hooks 16, and a trigger 18. A trigger 18 as used in the disclosure is any member that aids a user in manipulating the movable parts of the device. The handle 12 and fingers 14 may have channels or openings therein to allow the trigger 18 and any associated mechanics necessary to slide within them. The openings in the fingers 14 are adapted to allow the hair grips to move with respect to the fingers 14. In some embodiments the fingers 14 may form part of the handle 12. As described in more detail below, various embodiments of the device 10 include different types of hair grips. The hair grips may include hooks 16 (FIGS. 2A-8), pincers 116 (FIGS. 9-12), vacuum, tape, hook and loop fasteners, screw 216 (FIGS. 13-16), and chemical attachment. As shown, there are four fingers 14, each having a corresponding hook 16. It should be known that there may be three fingers 14 and hooks 16, or five fingers 14 and hooks 16, or any other number of fingers 14 and hooks 16 that a user deems is most efficient use of the space and most appropriate for the size/length of the laceration 8.

Figure 2A:
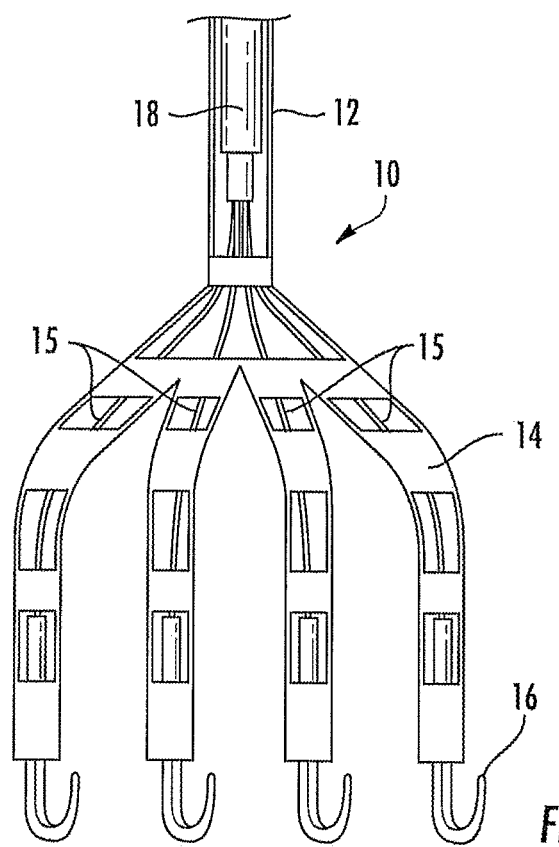
FIG. 2A is a bottom view of an embodiment of the hair grasping device.
Figure 2B:
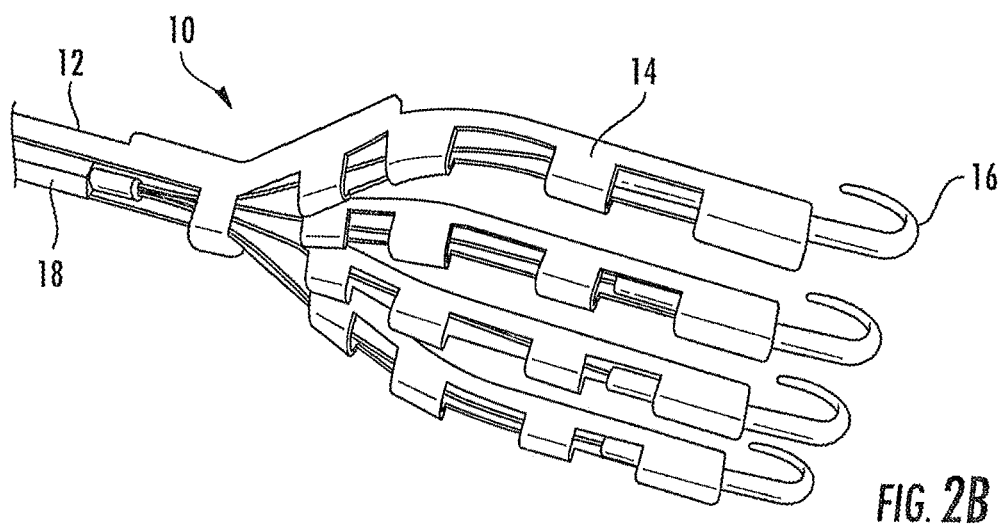
FIG. 2B is an isometric view of the hair grasping device shown in FIG. 2A.
Figure 3:
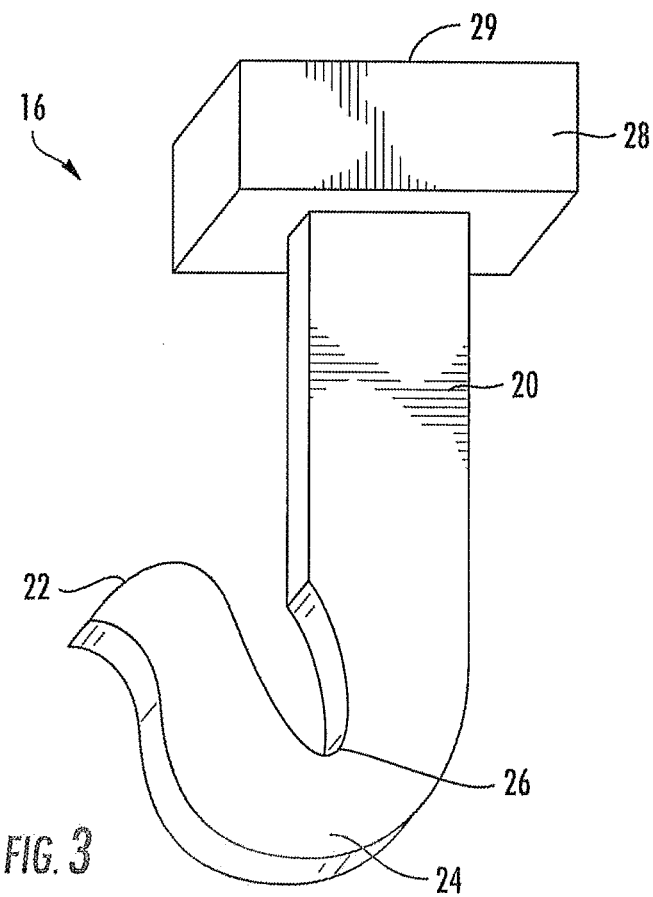
FIG. 3 is a detailed isometric view of a hook hair grasping device.

FIG. 3 shows an exemplary hook 16 of this particular embodiment in more detail. The hook 16 shown includes a base 20, a tip 22, and a bend 24. The hook 16 may have a notch or throat 26 that is sized to grasp and hold a certain amount of hair 4. In other embodiments the hook 16 may have a barb member (not shown) extending therefrom to grasp and hold the hair 4. The hook 16 may also have a connection portion 28 that allows the hook 16 to be connected to a cable 15 (FIGS. 2A & 2B). The cable 15 is operably combined with a trigger 18 to allow the user to move the hook(s) 16 between a hair grasping position and a hair holding position. The cable 15 can be comprised of, but is not limited to, stainless steel, titanium, nitinol, nylon. The connection portion 28 may also be sized and shaped such that it allows a landing 29 for a spring (not shown) which may bias the grasping mechanism in the hair grasping position.

Figure 4:
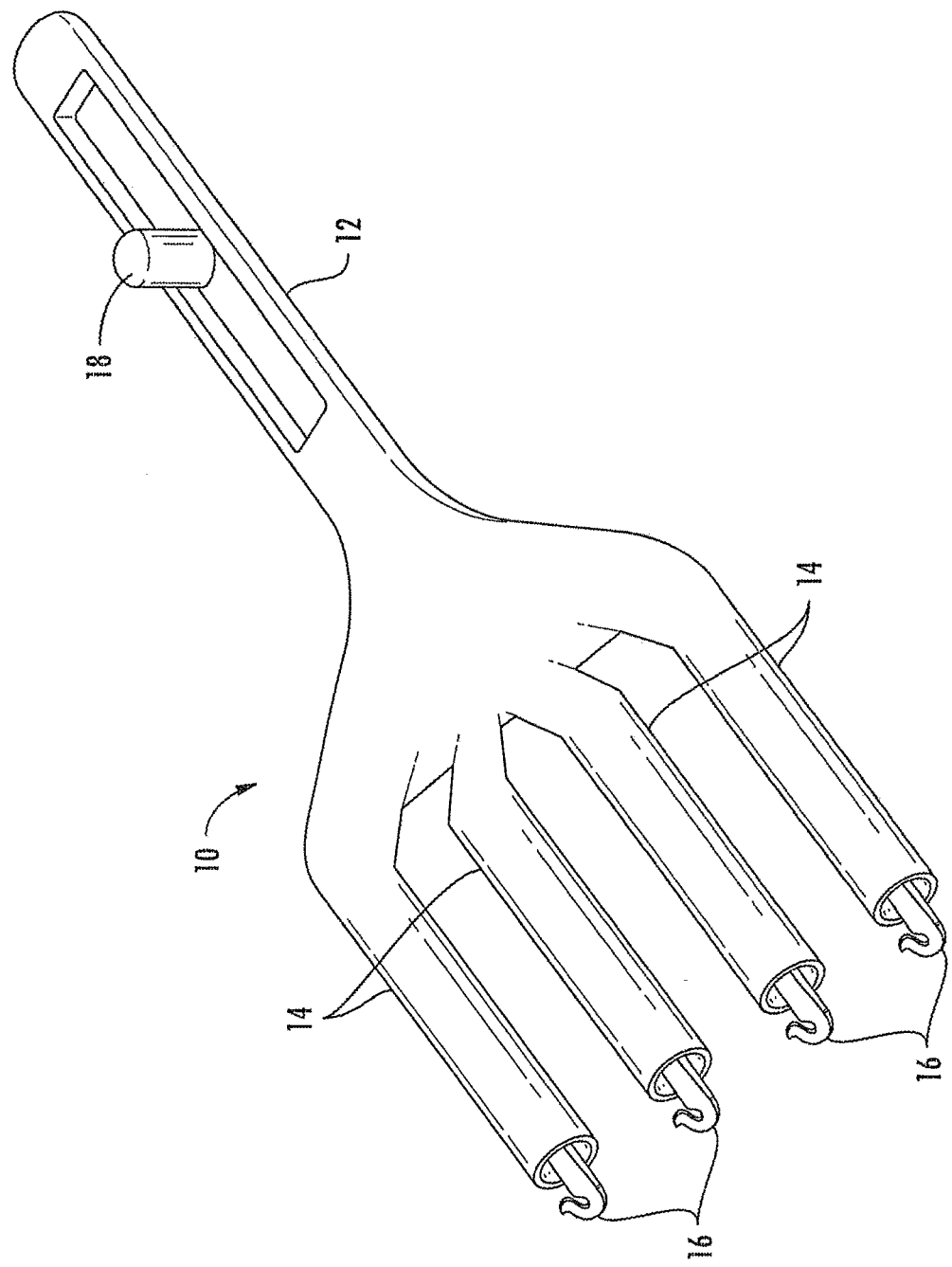
FIG. 4 is an isometric view of another embodiment of the hair grasping device.
Figure 5A:
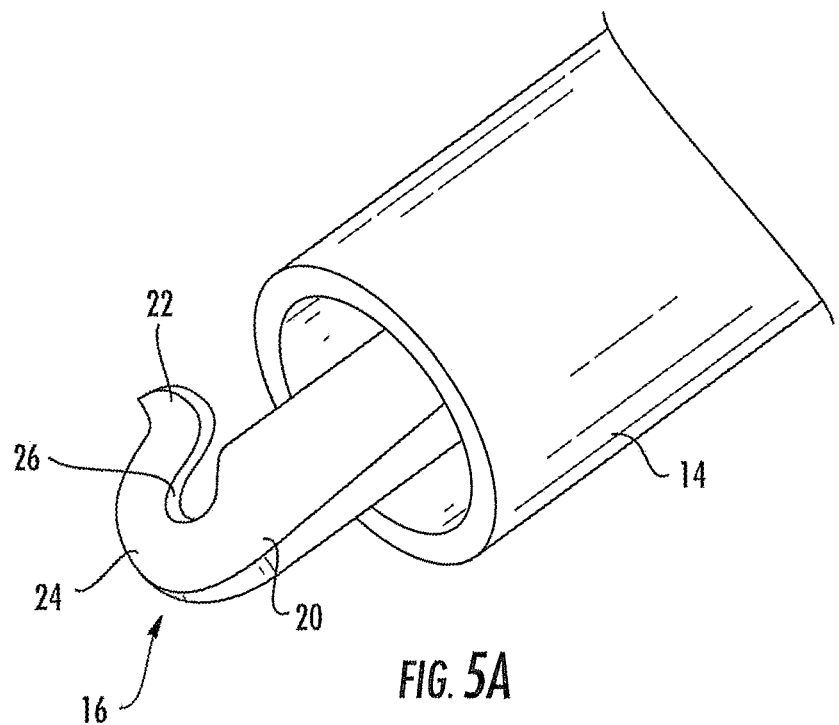
FIG. 5A is a close up isometric view of the finger and hook arrangement of the device shown in FIG. 4 in the hair grasping position.
Figure 5B:
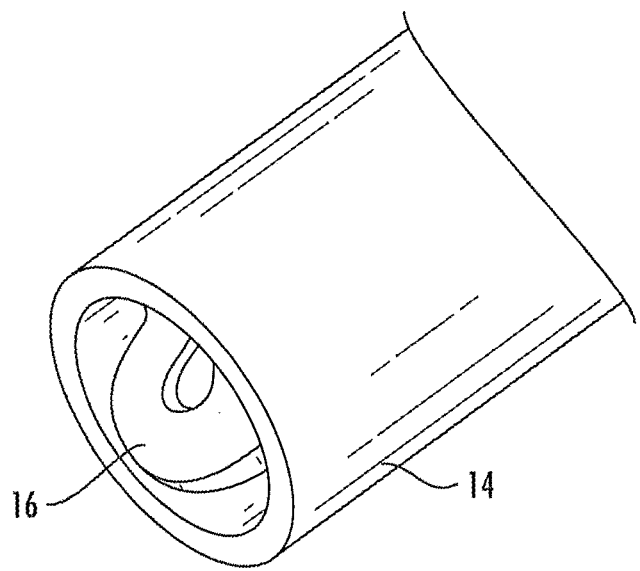
FIG. 5B is a close up isometric view of the finger and hook arrangement of the device shown in FIG. 4 in the hair holding position.
Figure 6:
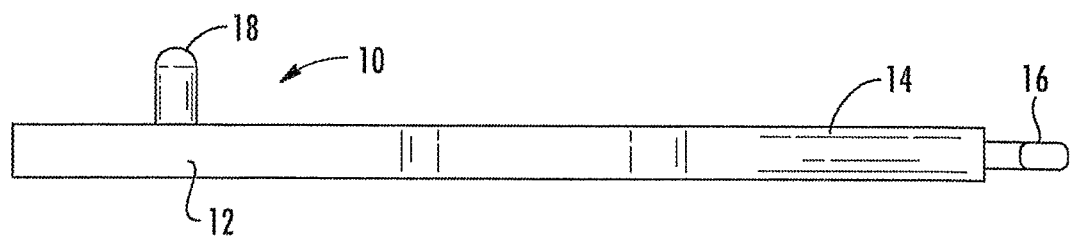
FIG. 6 is a side view of another embodiment of the hair grasping device.
Figure 7:
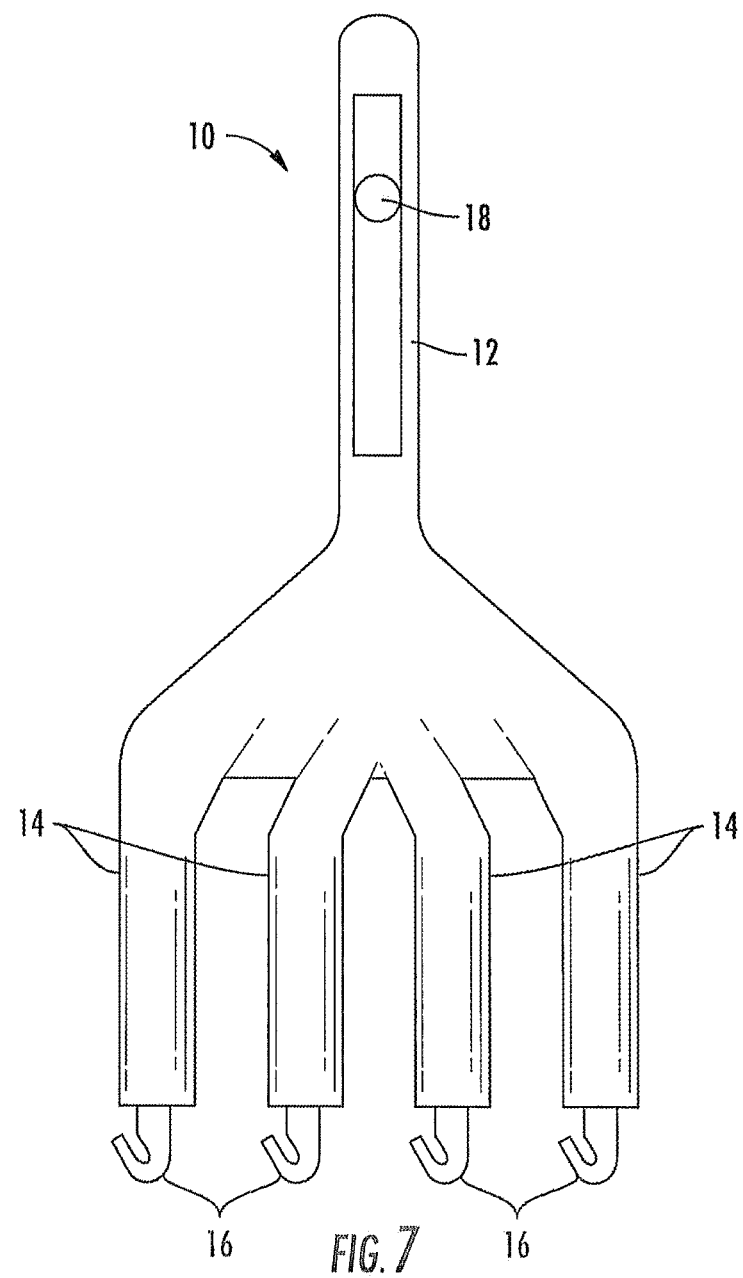
FIG. 7 is a top view of the hair grasping device shown in FIG. 6.

In the embodiment of FIGS. 2A-8, a user may grab the device 10 by the handle 12. The user may hold the device 10 with the handle 12 on one side of the laceration 8 and with the fingers 14 reaching across and to the opposite side of the laceration 8. The hair grips shown in FIGS. 2A-8 are hooks 16, which are placed such that the hooks 16 grab an amount of hair 4 from the opposite side of the laceration 8. The hooks 16 are positioned in the hair grasping position, as shown in FIGS. 2C, 4, and 5A, with tip 22, bend 24, and throat 26 open to grasp an amount of hair 4. Once an amount of hair 4 has been grasped by the hooks 16, the user may then actuate the trigger 18 within the handle 12 to move the hooks 16 from the hair grasping position to the hair holding position, as shown in FIG. 5B. A cable 15 has a first end combined with the trigger 18 and a second end combined with the hooks 16. The cable 15 may extend through openings in the handle 12 and fingers 14. As the user moves the trigger 18 in a direction away from the fingers 14, the hooks 16 are pulled by the cable 15 to correspondingly move in the same direction. This movement of the hooks 16 is such that the tips 22 are operably coupled with the end of the fingers 14 so that at least a portion of the hair 4 is secured between the hooks 16 and a portion of the fingers 14. Operably coupled in this respect means that the tips 22 and the fingers 14 interact to help prevent the amount of hair 4 from escaping the hook 16. In the embodiments shown in FIGS. 2A and 2B, the hair 4 is held against and outer surface of the fingers 14. The base 20 of the hook 16 is substantially inserted within the finger 14, but the bend 24 and the tip remain on the outside of the finger 14, essentially holding the hair 4 between the end of the finger 14 and the throat 26 of the hook 16. In the embodiment shown in FIGS. 4-7, the tips of the hooks 16 are fully retracted within the fingers 14 in the hair holding position as shown in FIG. 5B. A portion of the hair 4 is secured between the hook 16 and the inside wall of the fingers 14 so that the hair 4 is held in place by the tension between the hook 16 and the inside wall of the fingers 14. There may also be a pin or other feature (not shown) inside the fingers 14 which offers the opposing force with the hook 16.

Figure 2C:
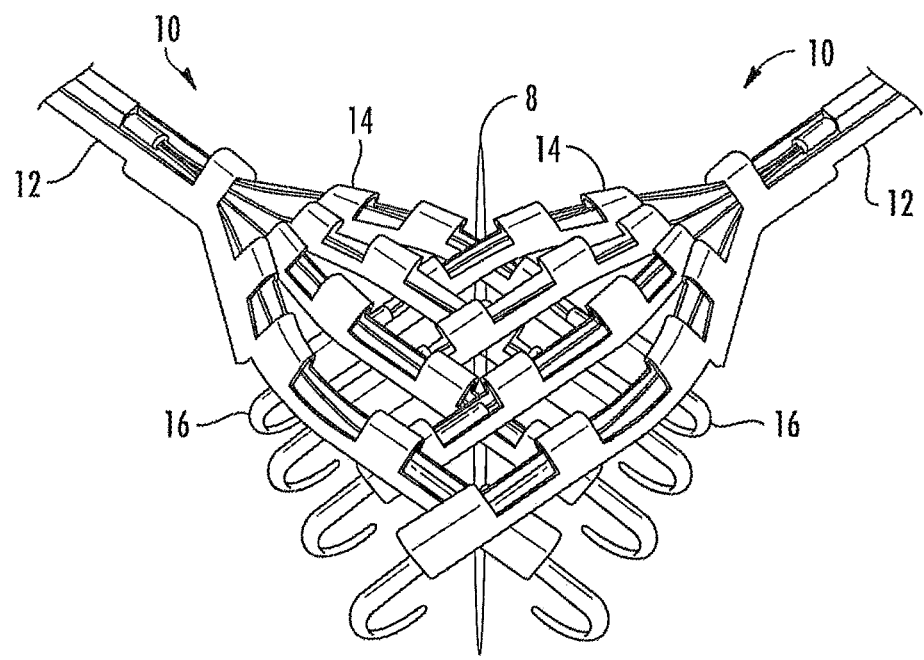
FIG. 2C is an isometric view of two hair grasping devices being used simultaneously.

There may further be a spring (not shown) within the fingers 14 that urges the hook 16 back into the hair grasping position when the trigger 18 is released. The spring may have an end that rests on the landing 29 of the hook 16. As shown in FIG. 2C, in some embodiments two devices 10 may be used at the same time to contemporaneously grab and pull hair 4 across the wound from opposite sides of the laceration 8. Further, the finger 14 may also include a cutting mechanism such as a blade to cut the hair 4 a predetermined distance from the throat 26 of the hook 16. As the hook 16 is pulled into the finger 14, the hair 4 may be pulled against the blade, thereby cutting the hair 4 at that point while still holding the hair 4 securely between the hook 16 and the finger 14. The cutting blade may be disposed within the finger 14 in such an area as to be not accessible by a user's fingers in normal use. The blade is described in more detail below with respect to FIGS. 33 and 34. Further, the trigger 18 may also include a detent such as a latch which secures the trigger 18 in its actuated position without the user needing to hold it in the hair holding position. This makes it easier for the user to apply glue or other material to the laceration 8. The detent or latch may further include a release for moving the components back to the hair grasping position when the user is ready to release the hair 4.

Figure 8:
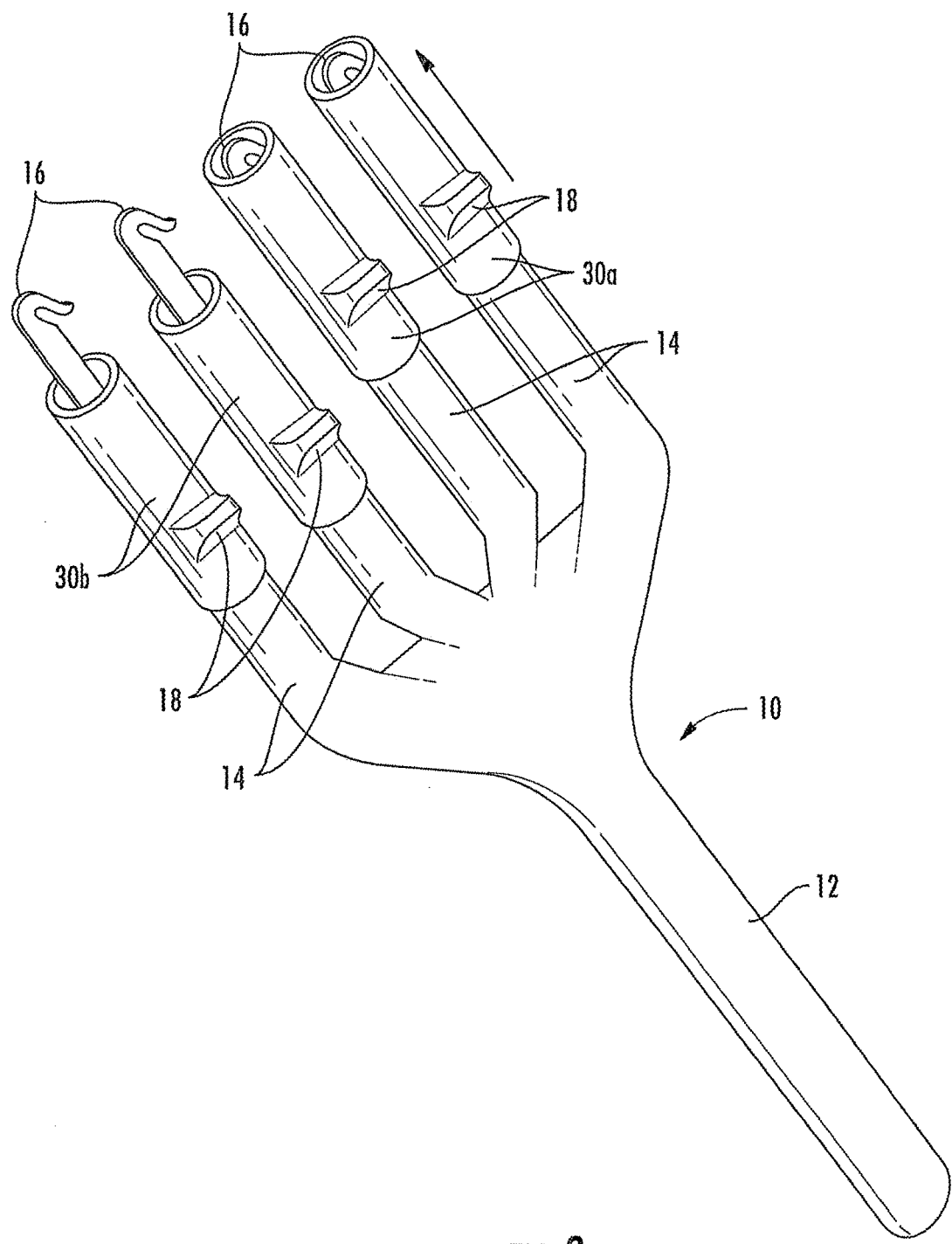
FIG. 8 is an isometric view of another embodiment of the hair grasping device.
Figure 9:
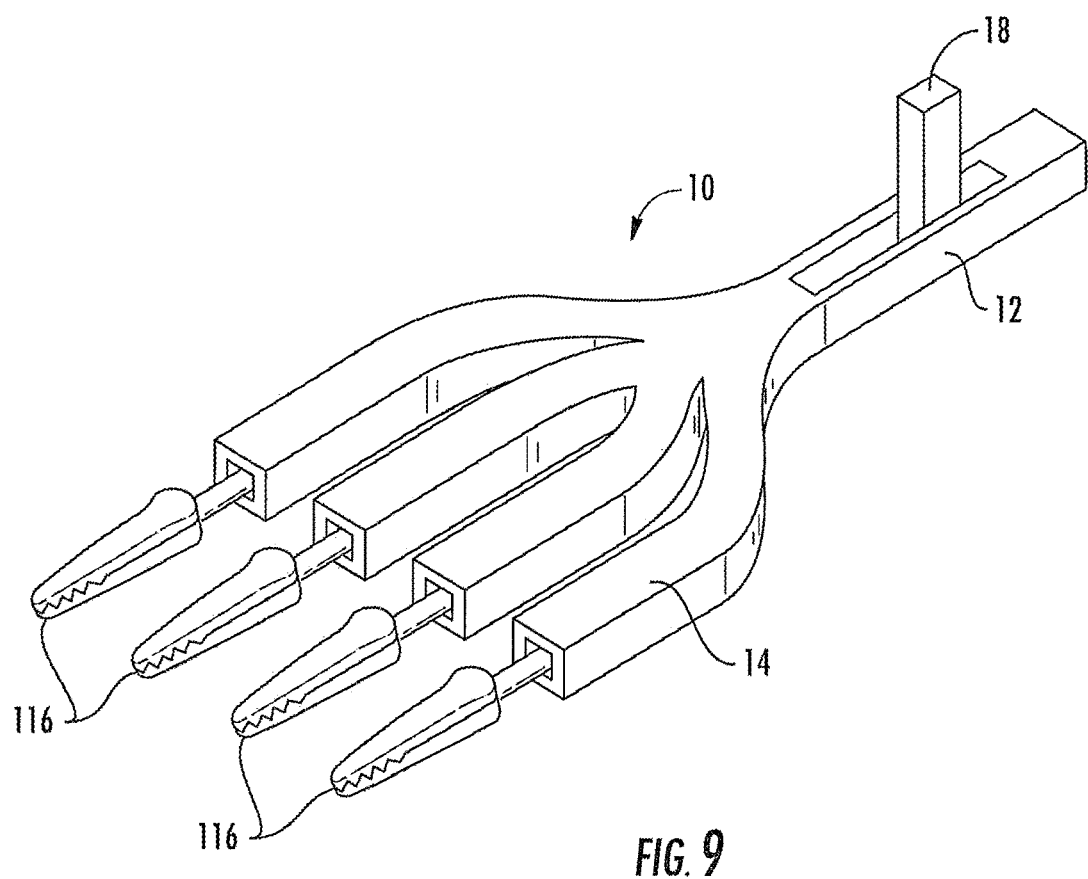
FIG. 9 is an isometric view of the hair grasping device of still another embodiment.
Figure 10:
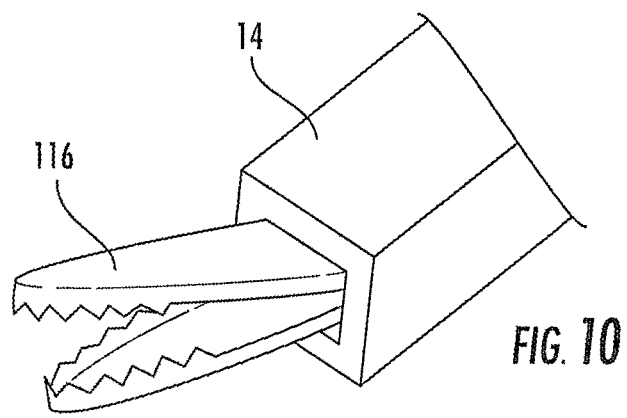
FIG. 10 is a close up isometric view of the finger and hook arrangement of the device shown in FIG. 9 in the hair grasping position.
Figure 11A:
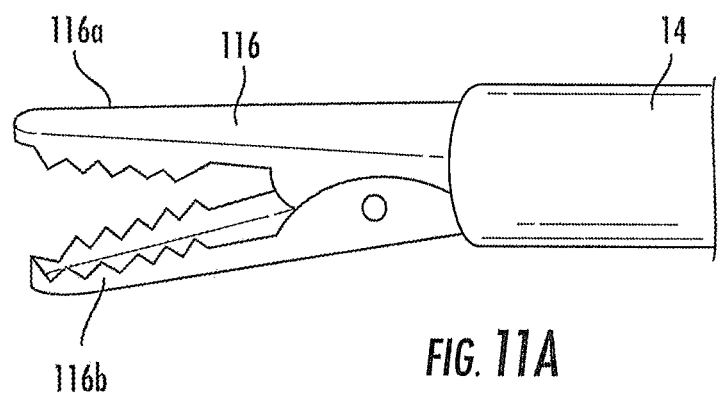
FIG. 11A is a close up isometric view of the finger and hook arrangement of the device shown in FIG. 9 in the hair grasping position.
Figure 11B:
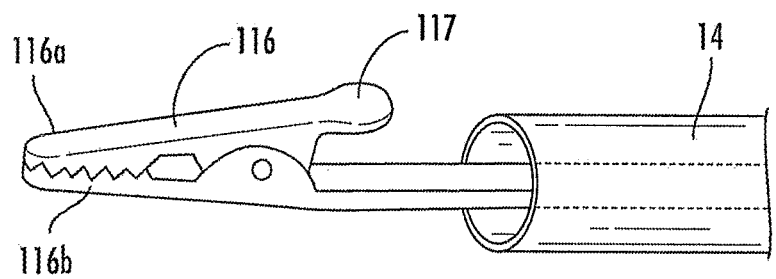
FIG. 11B is a close up isometric view of the finger and hook arrangement of the device shown in FIG. 9 in the hair holding position.

Turning now to the embodiment shown in FIG. 8, the fingers 14 and the hooks 16 are stationary with respect to one another. In this embodiment, neither the handle 12 nor the fingers 14 need to be hollow. In this embodiment, an extrusion 30 is movable over the fingers 14 between a hair grasping position and a hair holding position. The extrusions 30 may each have independent triggers 18 on them. These individual triggers 18 may be a separate piece attached to the extrusion 30, or may be created integrally with the extrusion 30. In this embodiment, extrusions 30a are in the hair holding position and extrusions 30b are in the hair grasping position. The user may grab an amount of hair 4 with the hair grips (shown as hooks 16) exposed and the extrusions 30 in the hair grasping position, and then use the triggers 18 to move the extrusions 30 to the hair holding position, with the hair 4 being held in place with tension between the hooks 16 and the inside wall of the extrusion 30. In another embodiment, extrusion 30 may not have openings therein, but rather may be a flat, slidable piece and not encircle the hook 16. The hair 4 may be held within the hook 16 and against the flat extrusion 30 and held in place.

FIGS. 9-12B show another embodiment of the hair grasping device 10. The basic configuration of the handle 12 and fingers 14 is similar to that described above. In this embodiment, the hair grip is an alligator clip 116. In this embodiment, the hair grasping position and the hair holding position are reversed from the above embodiments because the device 10 is in the hair grasping position when the alligator clips 116 are retracted and the hair holding position when the clips 116 are extended away from the fingers 14. As shown in FIGS. 11A and 11B, the alligator clips 116 may include an upper arm 116a and a lower arm 116b. The upper arm may further have a lever arm 117.

In the hair grasping position, lever arm 117 is forced to a closed position by the inner wall of the finger 114. When the lever arm 117 is forced closed, the arms 116a and 116b are correspondingly forced open. This allows the user to capture an amount of hair 4 between the arms 116a and 116b. In the embodiment shown in FIG. 12A, a trigger 18 is disposed in the handle 12 of the device 10 (similar to FIGS. 4, 7, and 9) to extend and retract the clips 116 between the hair grasping position and the hair holding position. However, in this embodiment, the structure must be such that pushing the trigger 18 toward the fingers 14 also pushes the grips 116 in the same direction. A rigid cable 15 (not shown) or other rigid member is used as before to transfer force between the trigger 18 and the hair grips.

Once the grips 116 are pushed far enough out of the fingers 14 so that the lever arms 117 are no longer constrained by the inner wall of the fingers 14, the arms 116a and 116b are urged closed to their hair holding position by a biasing force (such as a spring) within the clips 116. The clips 116 are adapted to hold any hair 4 captured between the arms 116a, 116b. The lever arm 117 may further have a downward ramp (not shown) which allows for the alligator clips 116 to be pulled back to their hair grasping position within the fingers 14 and release the captured hair without needing to individually open each clip 116 before reinserting them into the fingers 14.

Figure 12B:
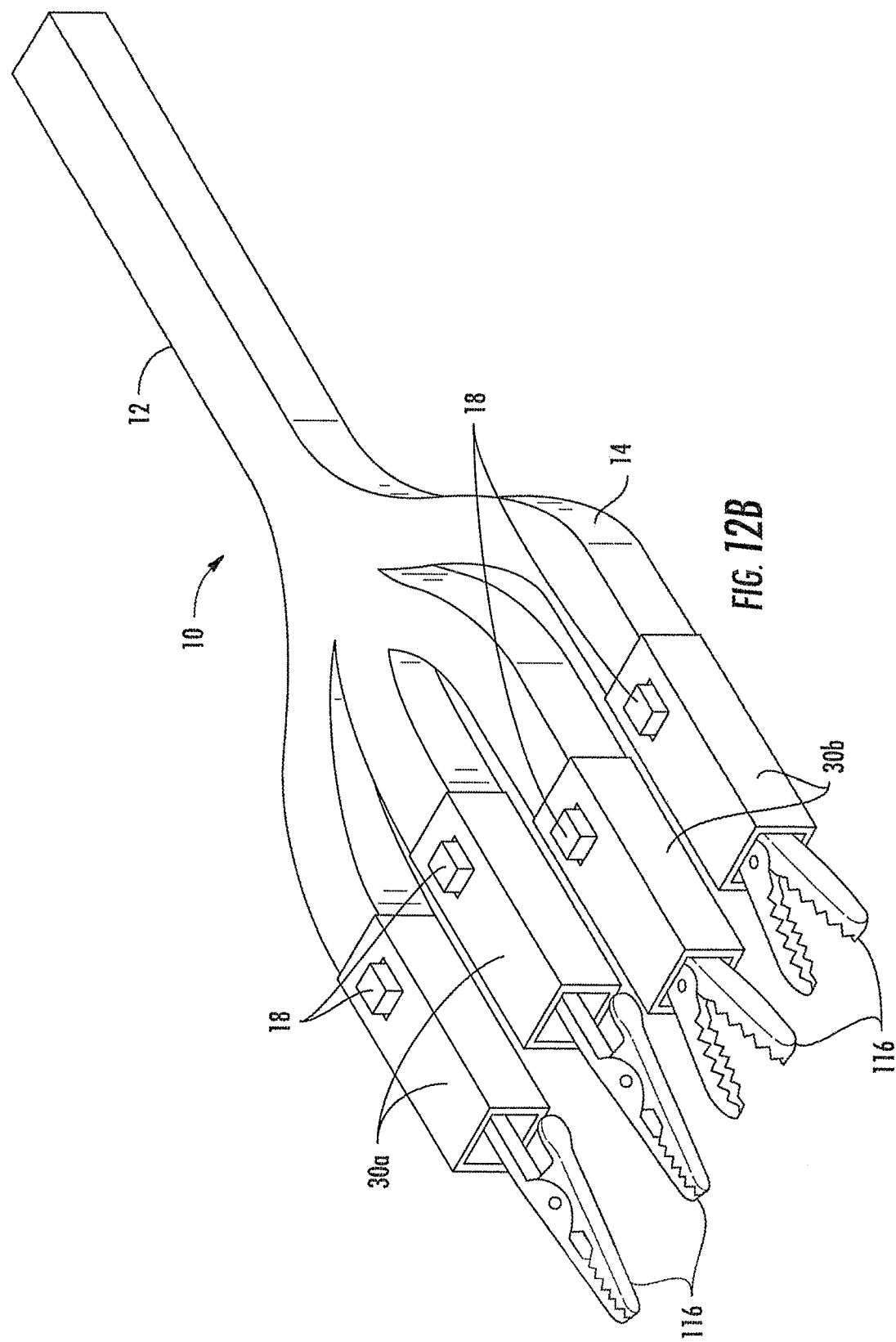
FIG. 12B is an isometric view of the hair grasping device of yet another embodiment.

As shown in FIG. 12B, the device 10 may include extrusions 30 similar to the extrusions 30 described above. Each extrusion 30 includes a trigger 18 adapted to allow movement of the extrusion 30 relative to the finger 14 and clips 116. The clips 116 are stationary with respect to the handle 12 and the fingers 14 so the movement of the extrusions 30 toward the handle 12 releases the clips 116 causing them to close to their hair holding position. Other embodiments may include a trigger 18 which allows movement of all of the extrusions 30 at the same time.

Some embodiments may include hair grips with are similar to the clips 116, but operate in reverse so that they are closed to a hair holding position by actuation of a trigger. These hair grips are similar to pincers.

Figure 13:
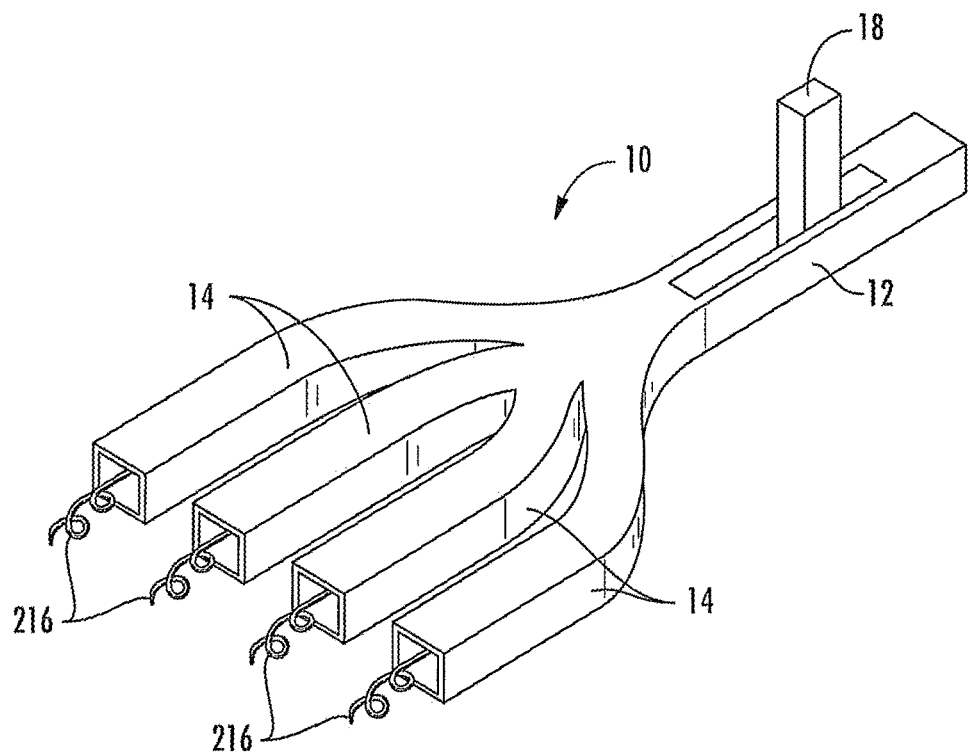
FIG. 13 is an isometric view of the hair grasping device of yet another embodiment.
Figure 14:
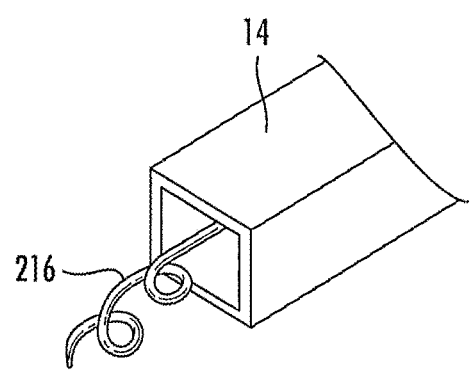
FIG. 14 is a close up isometric view of the grip and finger of the device shown in FIG. 13.

FIGS. 13-14 show an embodiment that is similar to that of FIGS. 4-7. In this embodiment, the grips are screw-shaped grips 216. The device 10 operates in much the same way as the embodiment of FIGS. 4-7, however, instead of hooking an amount of hair 4 in a throat 26 of a hook 16, the user works the screw grip 216 to capture an amount of hair in the threads of the screw such that the hair 4 is wrapped and captured around the screw 216. In the hair holding position, at least a portion of the screw grip 216 retracts within the finger 14 to hold the hair 4 in place by tension between the screw 216 and the fingers 14.

Figure 15:
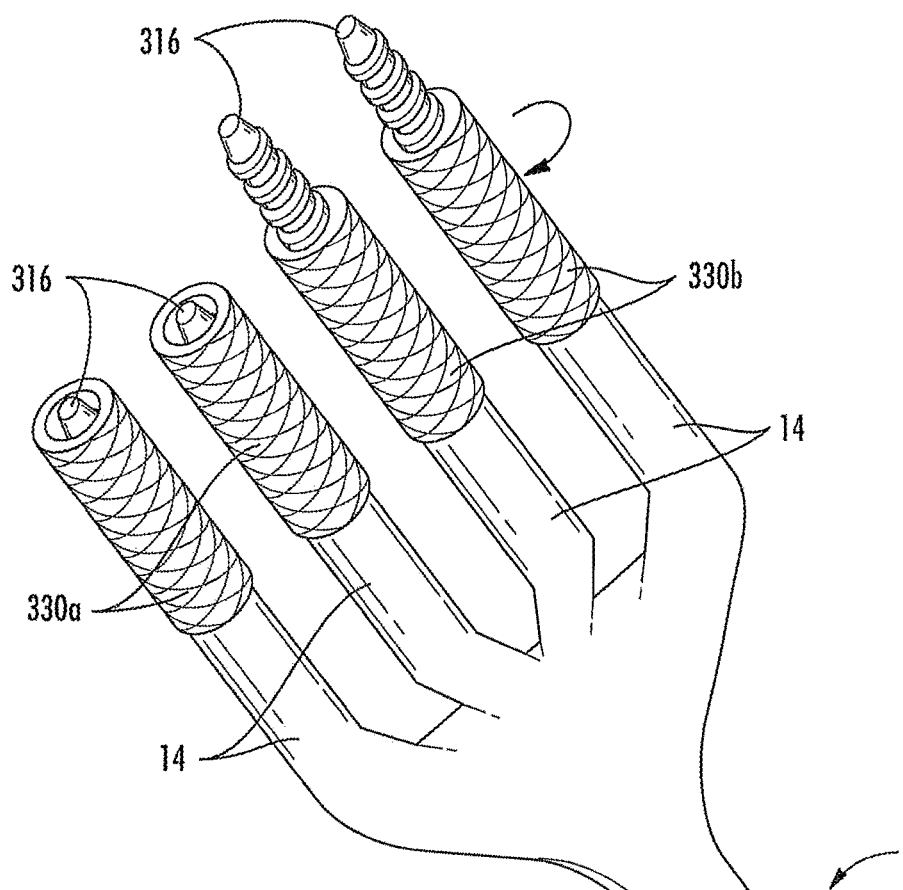
FIG. 15 is an isometric view of the hair grasping device of another embodiment.
Figure 16:
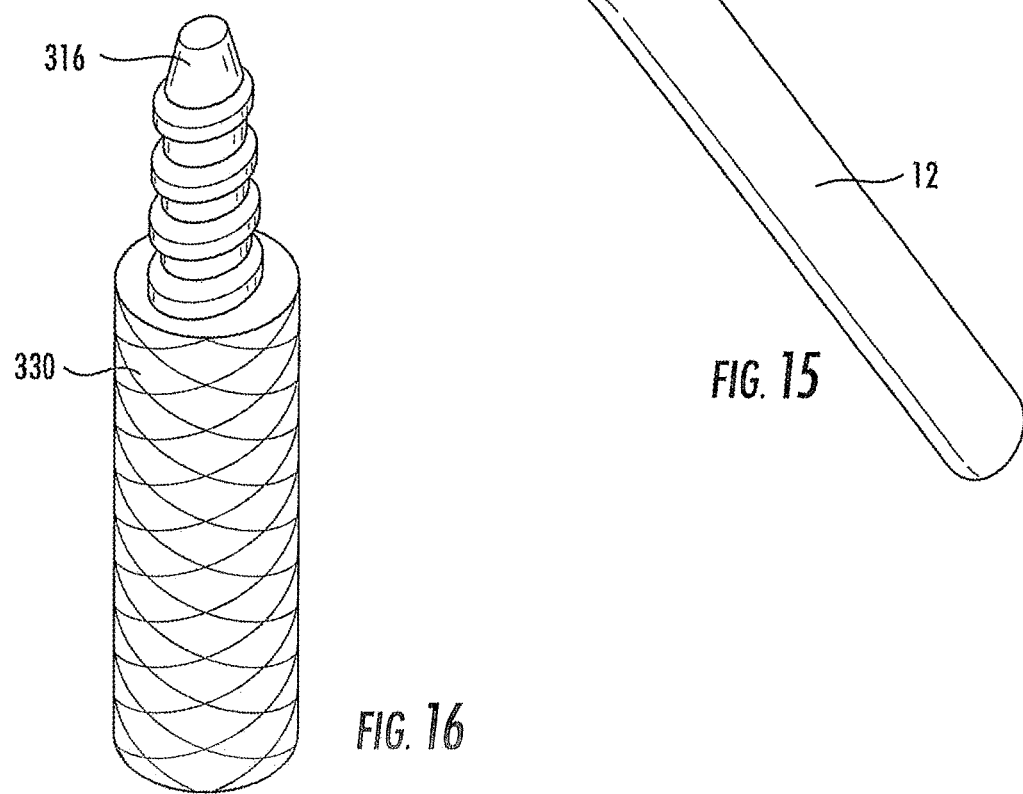
FIG. 16 is a close up isometric view of the grip and finger of the device shown in FIG. 15.

FIGS. 15-16 show an embodiment similar to the one described in the previous paragraph, however, the hair grip has external threads. The threaded grip 316 is linearly movably disposed within an internally threaded extrusion 330 that is rotatably disposed on the finger 14. In this embodiment, the trigger may be defined as the external surface of the extrusion 330, as that is the part manipulated by the user. The threaded grips 316 are externally threaded and associated with the internal threads of the extrusions 330. In the hair grasping position as shown by extrusions 330*b*, the threaded grips 316 are extended beyond the end of the extrusions 330. In the hair holding position, the threaded grips 316 are disposed within the extrusions 330. The hair 4 is held in place by tension between the threaded grips 316 and the interior walls of extrusions 330.

Figure 29:
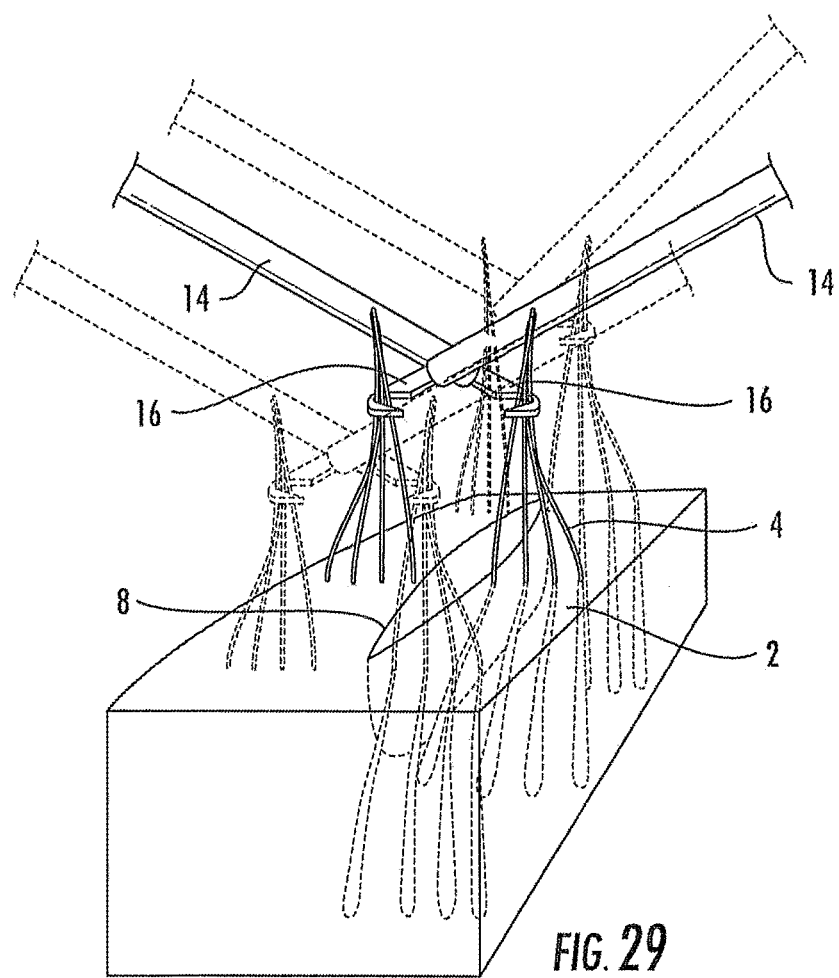
FIG. 29 is a schematic isometric view of the fingers and hooks of an embodiment of the hair grasping device.

In all of the embodiments of FIGS. 2-16, one device 10 may be used in conjunction with a second device 10 as shown in FIGS. 2C and 29. The fingers of each device 10 may be spaced apart such that the fingers of each device 10 fit between the fingers 14 of the second device 10, so that the devices 10 may be used simultaneously to grab an amount of hair 4 from one side of a laceration 8 and pull the hair 4 to an opposite side of the laceration 8. The laceration 8 may be closed using an adhesive glue 5, tying the hair 4 together, or held together in some other fashion to hold the laceration 8 closed.

Figure 17:
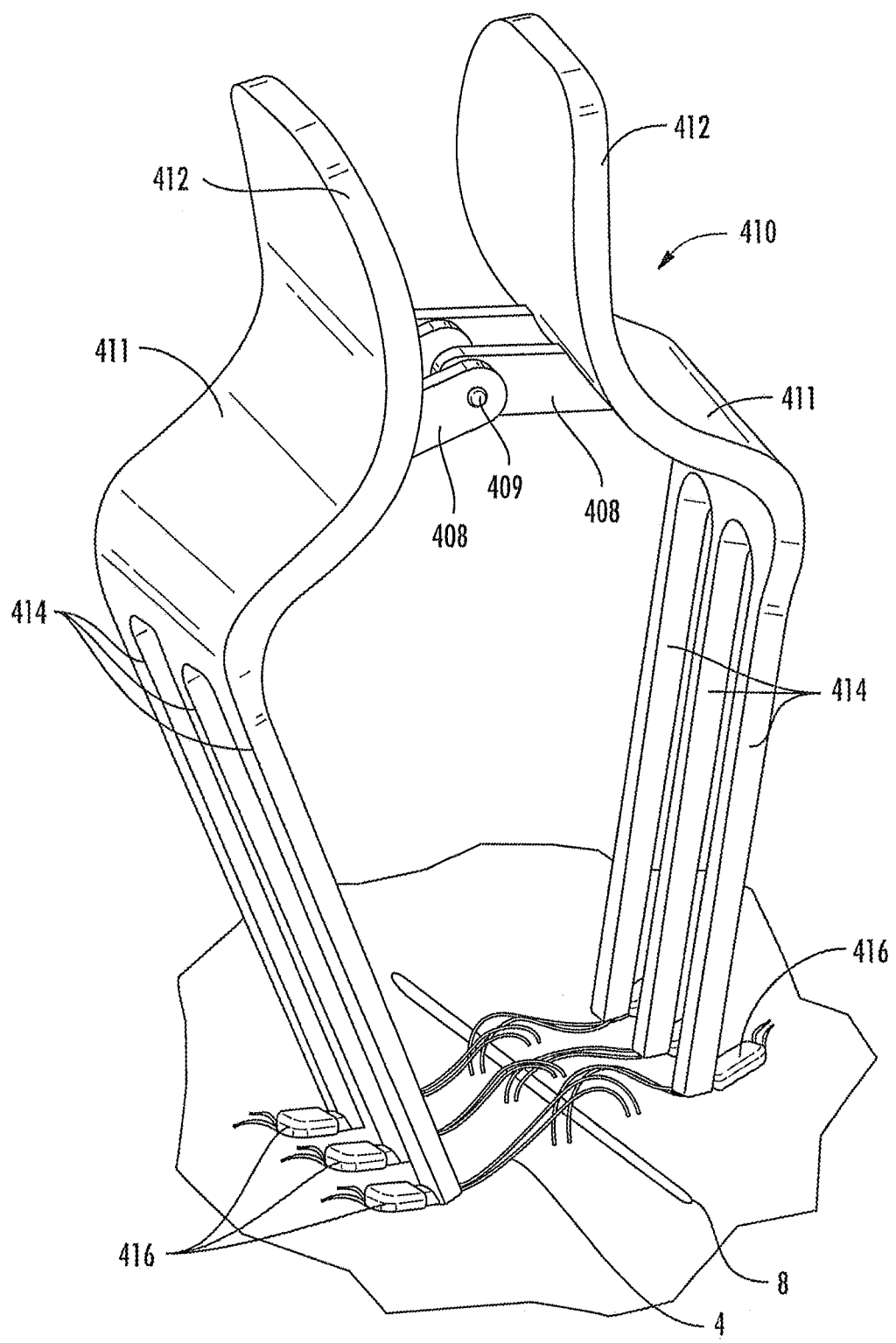
FIG. 17 is an isometric view of the hair grasping device of another embodiment.
Figure 20:
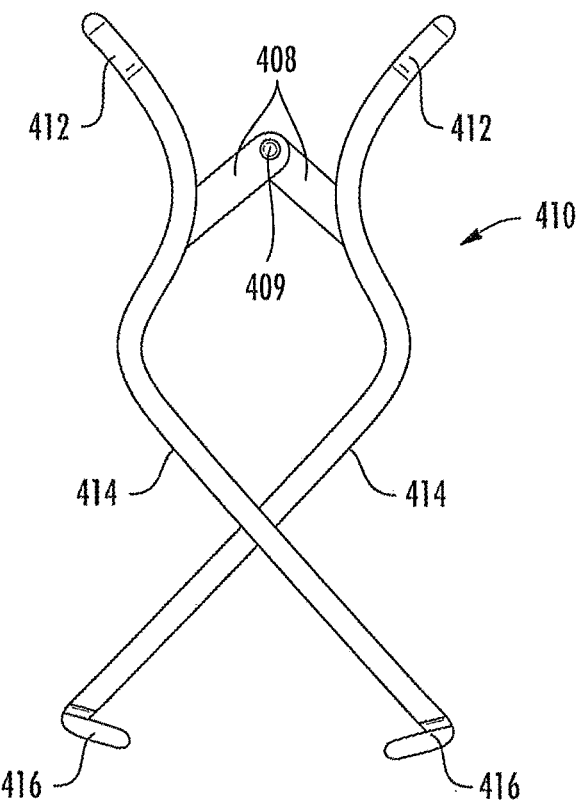
FIG. 20 is a side view of the hair grasping device of the shown in FIG. 17 in a hair grasping position.
Figure 21:
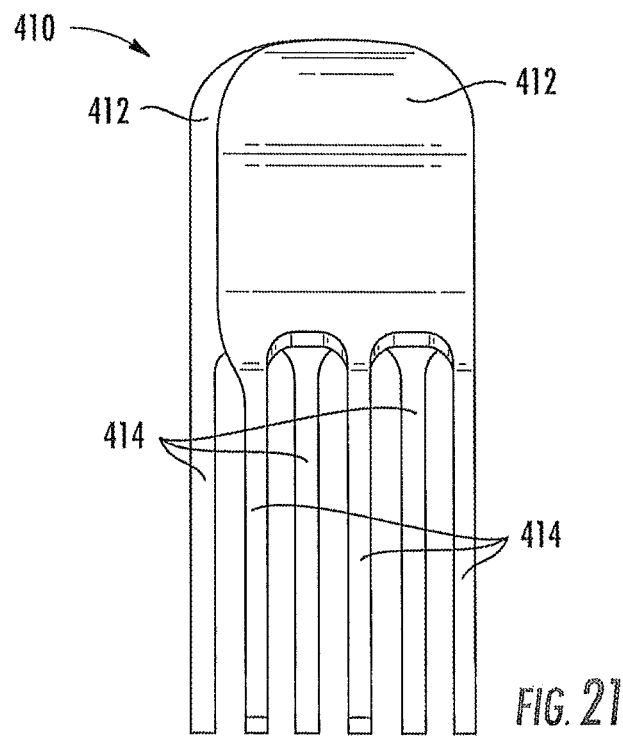
FIG. 21 is a front view of the hair grasping device of the shown in FIG. 17.

FIGS. 17-23 show an embodiment wherein a single device 410 includes opposing fingers 414 adapted to grab an amount of hair 4 on both sides of the laceration 8 at the same time and pull each respective amount of hair 4 across the laceration 8 to the other side. In this manner, the device 410 disclosed in this embodiment may be operated by a user using a single hand. In FIG. 17, the hair grasping device 410 has arms 411 which have similar structure to the devices described above. Two arms 411 are substantially identical in structure and are placed opposite one another. The two arms 411 are connected by and rotate with respect to one another about lever arms 408. The lever arms 408 may further include a pin 409 which holds the two arms 411 together and defines the axis about which each arm 408 rotates. There may further be a spring (not shown) that urges the device into the hair grasping position. The hair grasping position in this embodiment is with the fingers 414 of the two arms 411 in a crisscross configuration as shown in FIG. 20. FIG. 17 shows the device 410 in the hair holding position.

Figure 18:
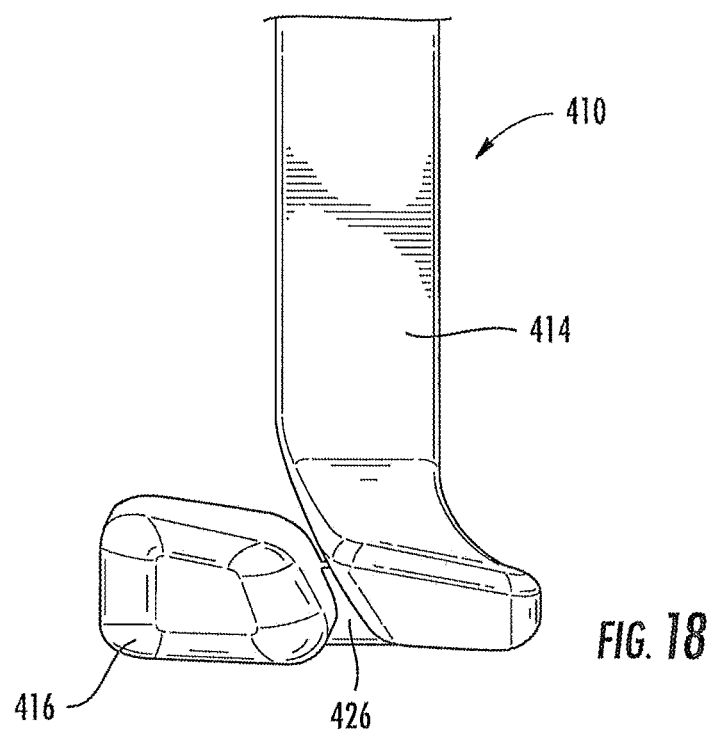
FIG. 18 is a close up isometric view of the grip and finger of the device shown in FIG. 17.
Figure 19:
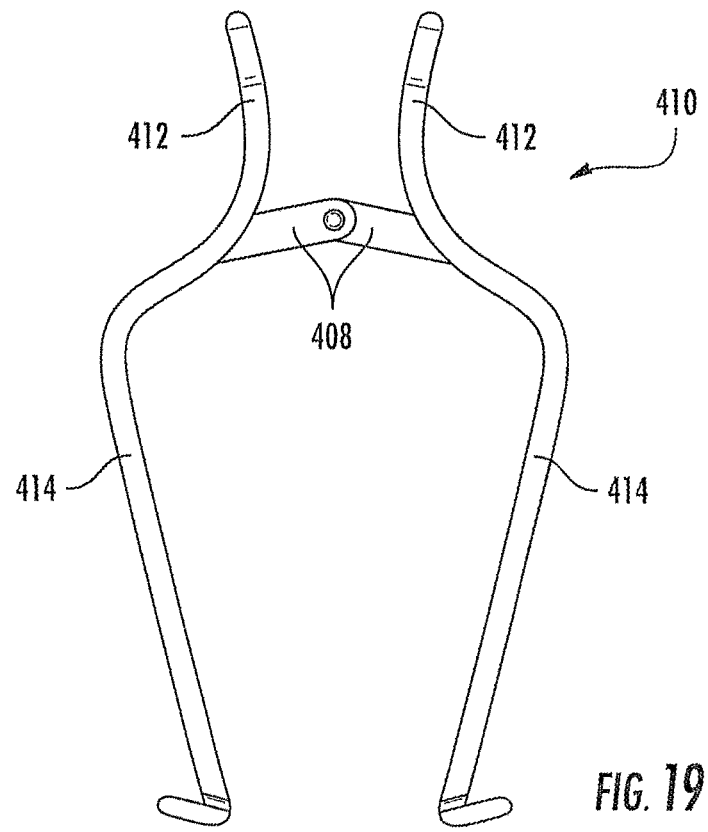
FIG. 19 is a side view of the hair grasping device of the shown in FIG. 17 in a hair holding position.

Turning now to FIG. 18, the device 410 has fingers 414 with hair grips on the ends of each of the fingers 414. The hair grips may include the hooks 16 or screw-shaped grips 216 described above. As shown, the grips 416 include a throat 426 defining a space between the grip 416 and the finger 414. The user may use one hand to grab the device 410. The user may place the device 410 such that fingers 414 from each of the arms 411 are lined up on opposite sides of a laceration 8. The user may then use a small twist motion to move an amount of hair 4 into the throat 426 of either side of the fingers 414. The twist motion may be necessary as the openings of the throat 426 face opposite directions when the device 410 is in use. The user may then squeeze the handles 412 of the two arms 411 together, which allows the fingers 414 of each arm 411 to cross to the opposite side of the laceration 8, as shown in FIG. 17. The user may then use these amounts of hair 4 to close up the wound. In another embodiment, an extrusion having an opening therein may be added to the fingers 414 to move relative to the fingers 414 and pinch the hair 4 in place, similar to the extrusions disclosed in the embodiments described above.

Figure 22:
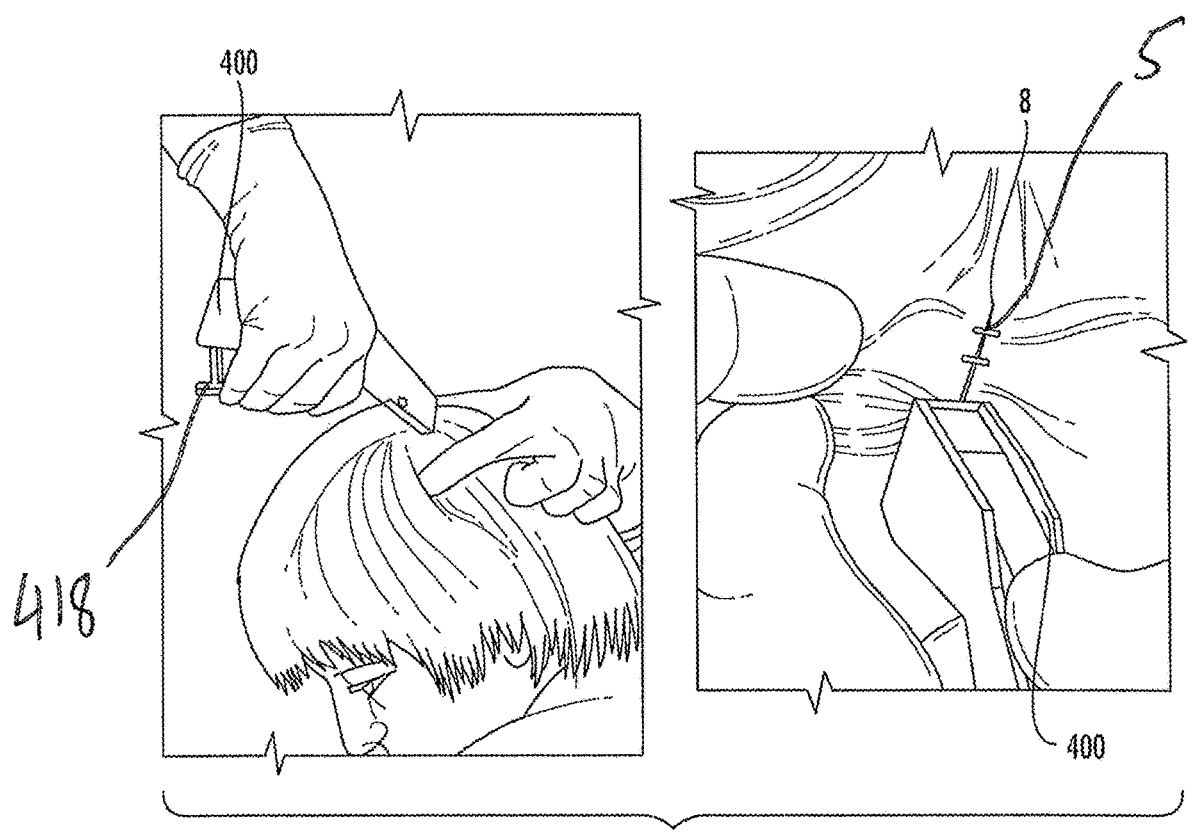
FIG. 22 is an isometric view of another embodiment of the hair grasping device which includes a single pair of opposing arms.
Figure 23:
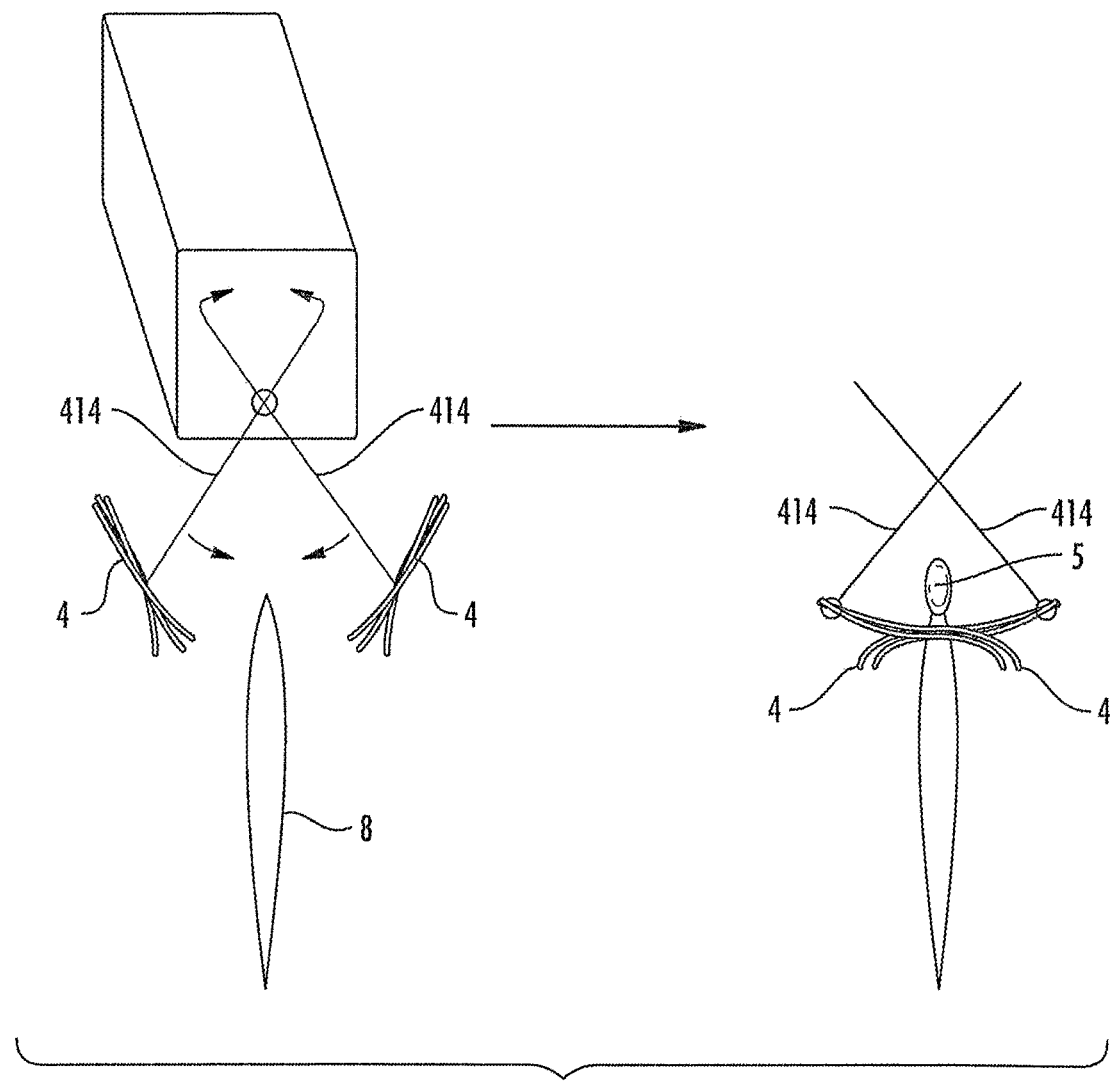
FIG. 23 is a schematic of the device shown in FIG. 22.

Additionally, as shown in FIGS. 22 and 23, a handheld device 400 may include similar structure as that shown in FIGS. 17-21, however with single fingers 414 on either side of the arms 411. The fingers 414 may be enclosed within a housing as shown in FIG. 22. The user may simply place the device 400 over a portion of the laceration 8 and actuate a trigger 418 to cross the fingers 414 thereby forcing the amounts of hair 4 across the laceration 8. The device may have a glue 5 reservoir (not shown) which automatically applies an amount of glue 5 to the closed laceration 8 after the hair has been crossed and the laceration 8 pulled together, as detailed in FIG. 23. The user may then move on to the next portion of the laceration and close the wound sequentially.

Figure 24:
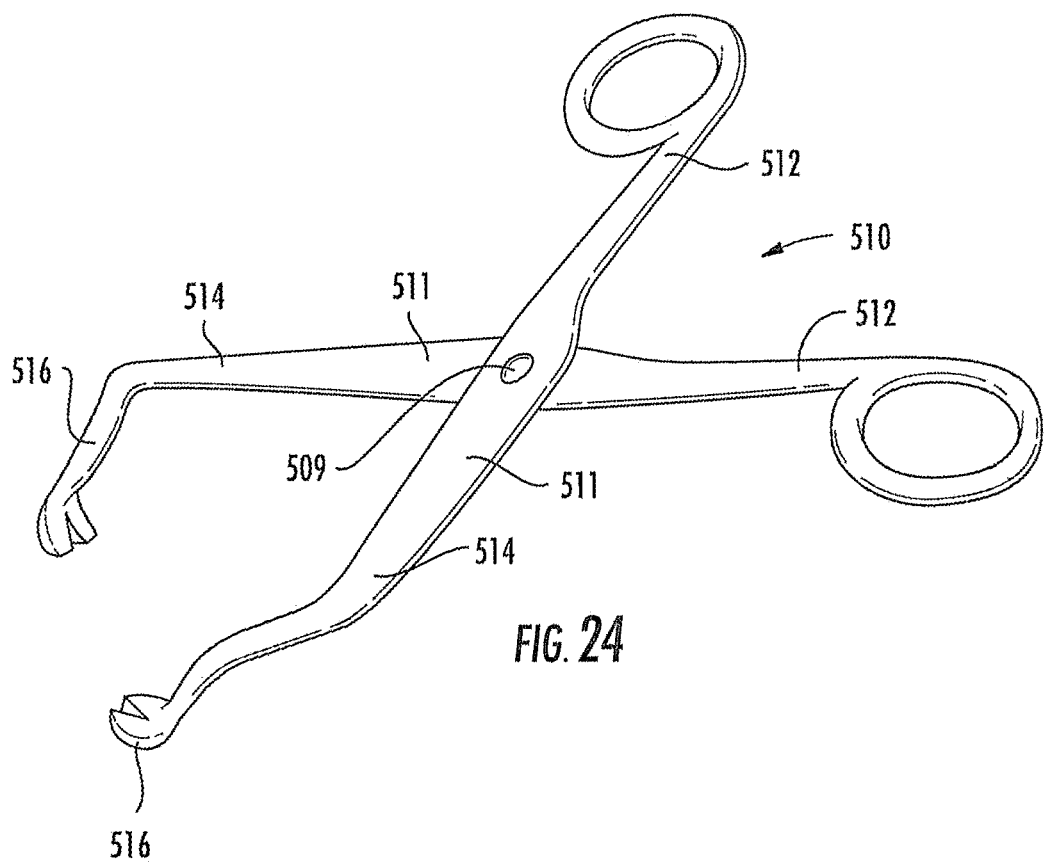
FIG. 24 is an isometric view of another embodiment of the hair grasping device in the hair grasping position.
Figure 25:
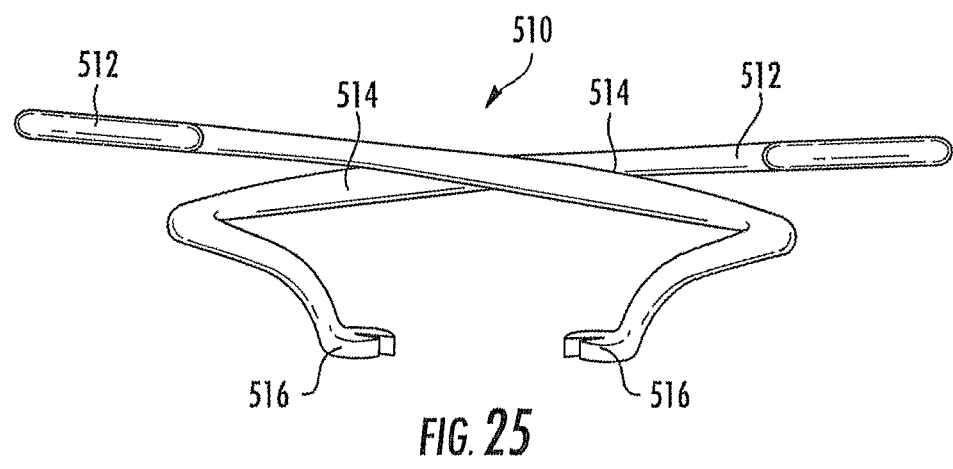
FIG. 25 is a side view of the hair grasping device shown in FIG. 24.
Figure 26:
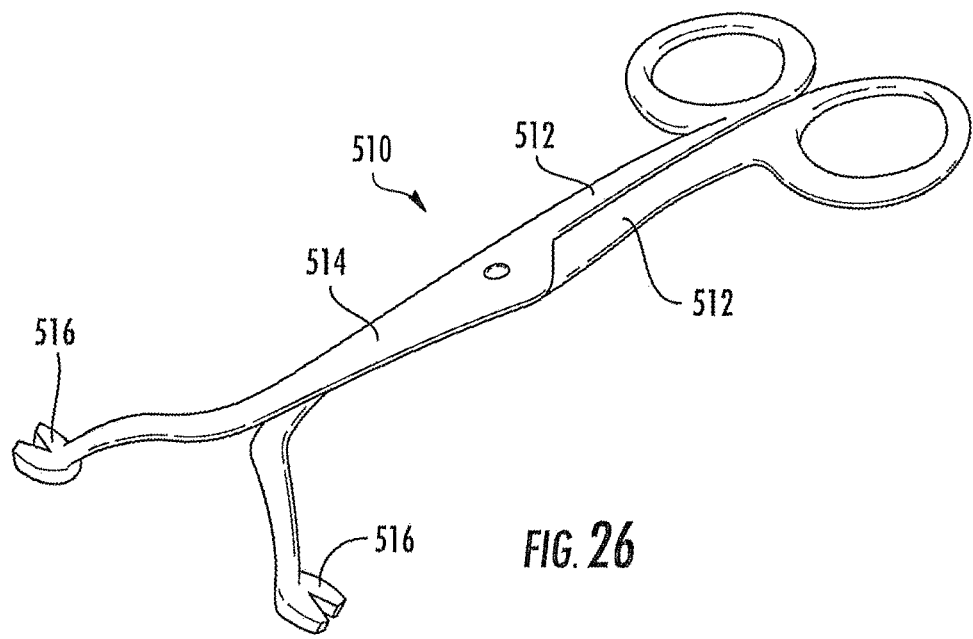
FIG. 26 is an isometric view of the hair grasping device shown in FIG. 24 in the hair holding position.
Figure 28:
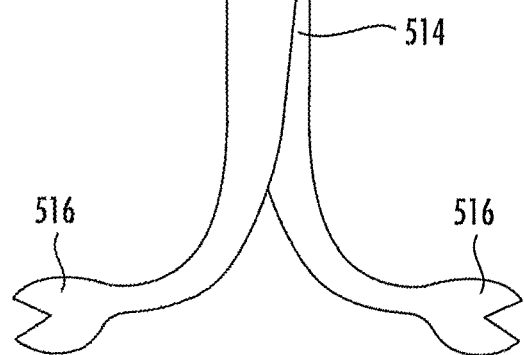
FIG. 28 is a close up side view of the grips and fingers of the device shown in FIG. 24.
Figure 27:
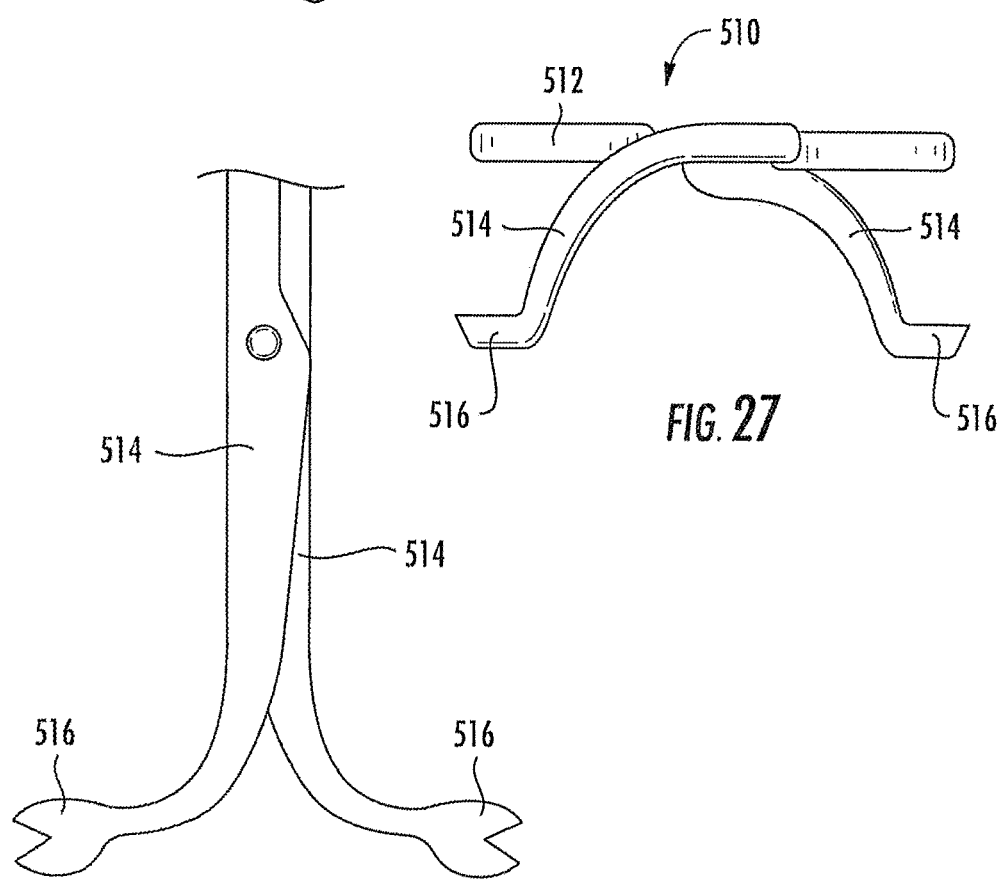
FIG. 27 is an end view of the hair grasping device shown in FIG. 24.

FIGS. 24-28 show another embodiment of the device 510 which may be operated by a single hand of a user. In this embodiment, the device 510 is a scissor-like configuration. The device 510 may include a pair of arms 511 connected by and rotatable about a pin 509. In the hair grasping position as shown in FIG. 24, the user holds the handles 512 apart, which also holds the grips 516 apart, and positions the grips 516 on either side of the laceration 8. The user then moves the device 510 to the hair holding position as shown in FIG. 26, pulling amounts of hair 4 from each side of the laceration to the opposite side. The user may then use their other hand to apply glue 5 or other material to close that portion of the wound, before moving on to closing to another portion of the laceration 8.

Figure 30A:
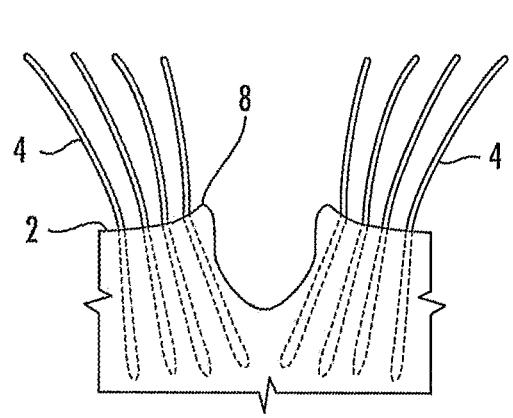
FIGS. 30A-30D are cross-sectional schematic views of a laceration of a patient as it is being closed using the device of an embodiment of the hair grasping device.
Figure 30B:
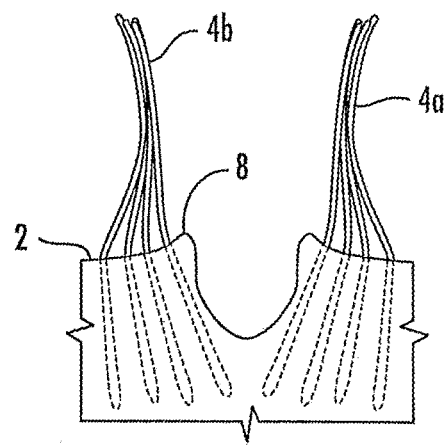
Figure 30C:
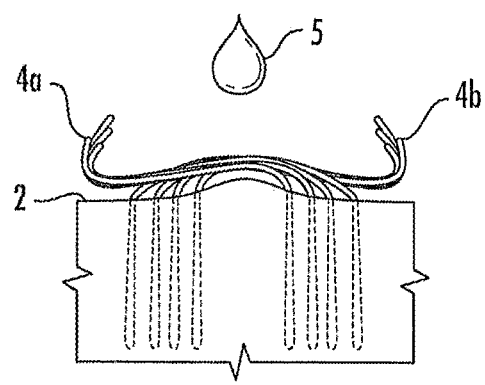
Figure 30D:
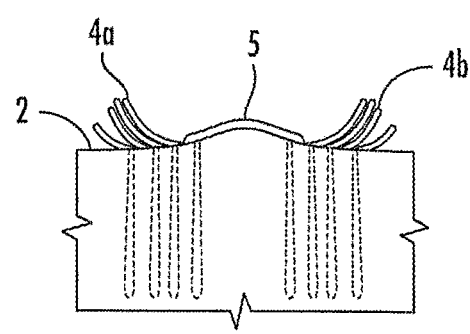

Using any of the above described techniques, the hair apposition technique may be efficiently used to save the user and the patient time, discomfort, and expense. FIGS. 29-30D show in detail how the devices 10, 410, and 510 may aid the user in accomplishing the technique. FIG. 29 shows the fingers 14 of a device and the respective hair grips that are associated with the fingers 14. It should be noted that the fingers 14 and hair grips could apply to any of the fingers 14 or hair grips disclosed in any of the above embodiments.

As shown in FIG. 29, the hair grips grab an amount of hair 4 on opposite sides of a laceration 8. In some embodiments, two devices may be used at the same time to simultaneously pull hair 4 from opposite sides of the laceration 8 across the laceration 8. FIG. 30A shows a basic configuration of the hair 4 before the device 10 is presented to the area. FIG. 30B shows a basic configuration of the area after the hair 4 has been grasped by the device 10. FIG. 30C shows that when the opposite sides of the device are moved across the laceration 8, the hair pulls the laceration 8 closed, closing the wound. An amount of glue 5 or other material is presented to the area to hold it closed. Finally, once the glue 5 has settled and dried, the laceration 8 is held closed by the crossed amounts of hair 4 and held by the glue 5.

Figure 31:
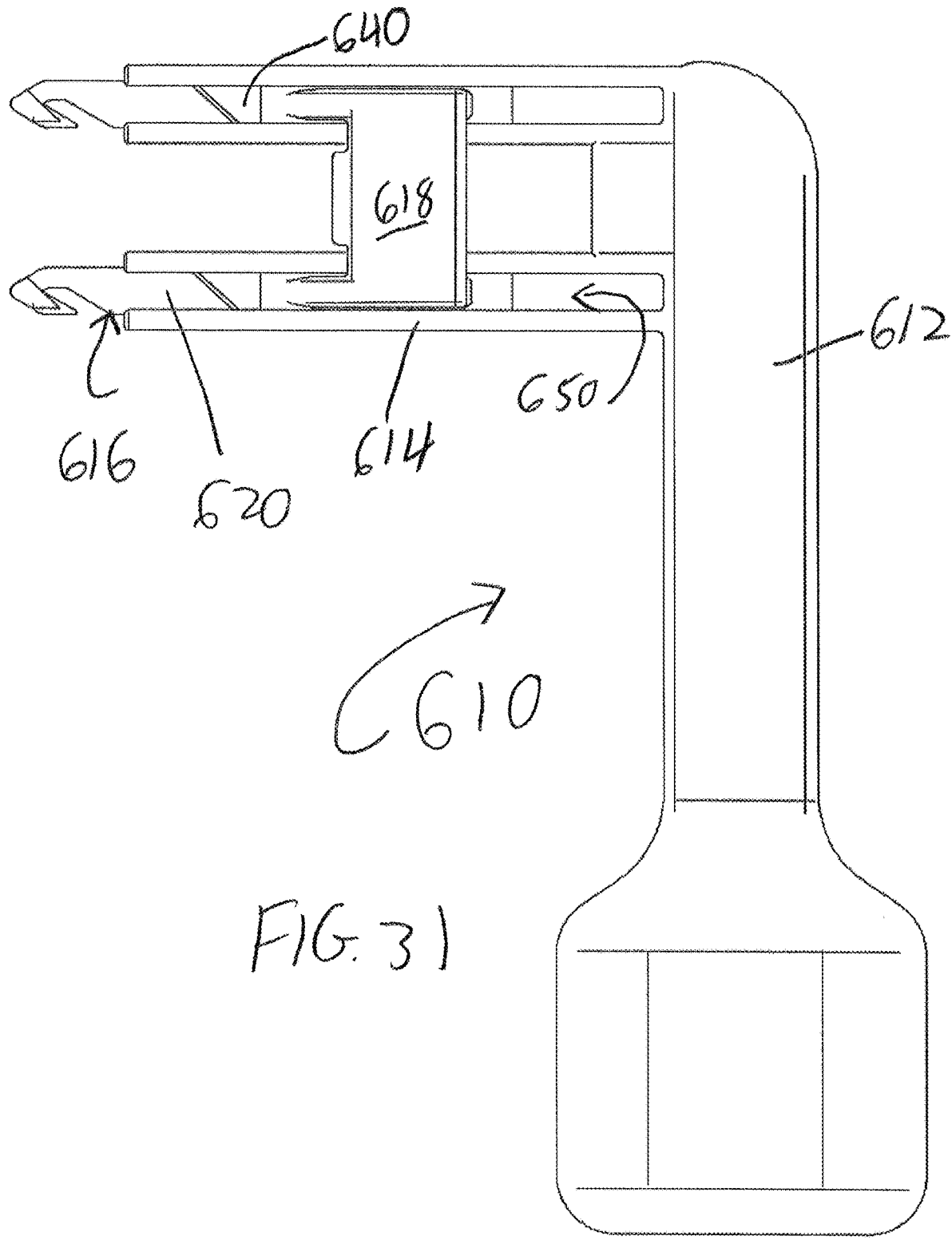
FIG. 31 is an top view of another embodiment of the hair grasping device showing the hooks in the hair grasping position.
Figure 32:
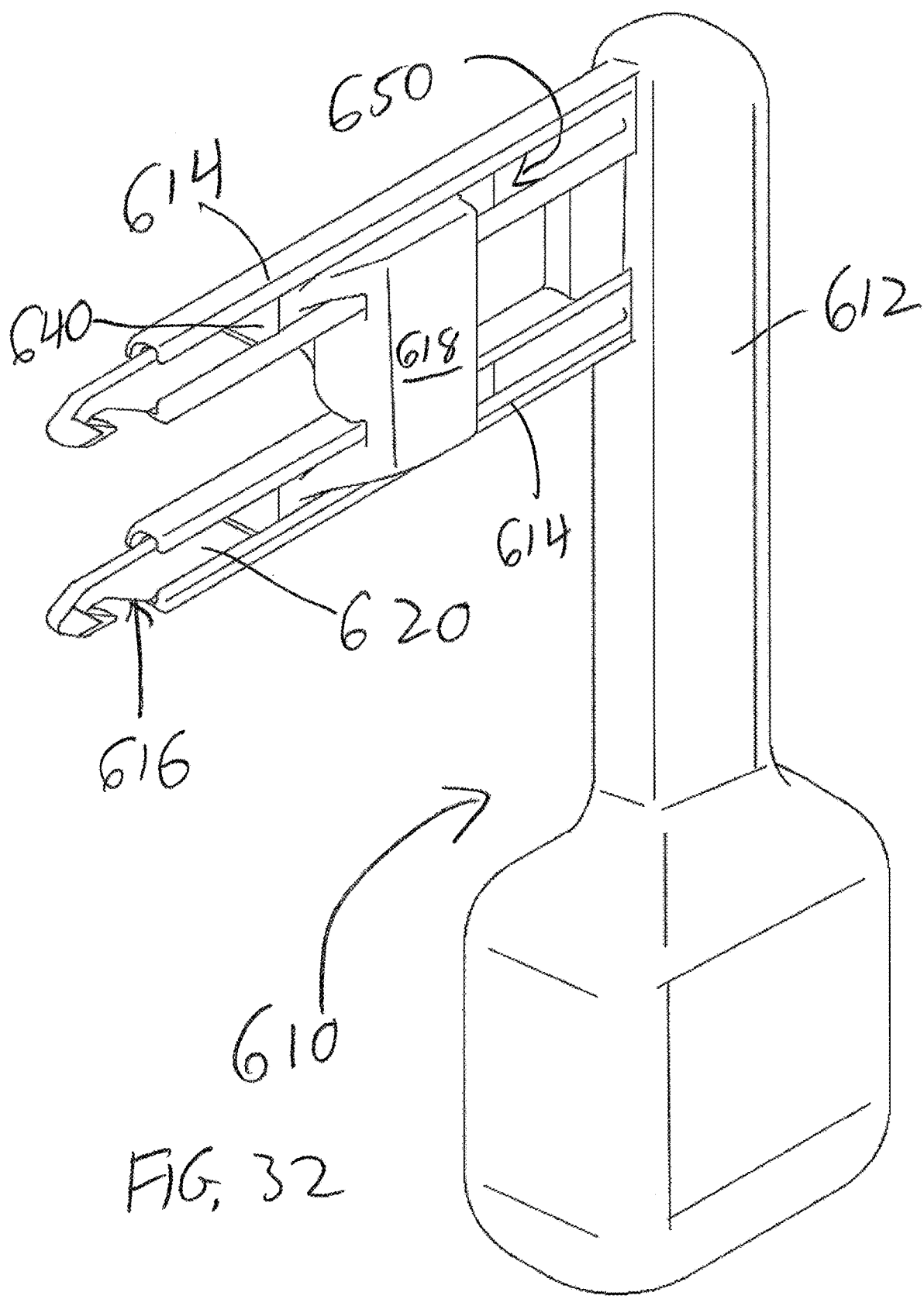
FIG. 32 is an isometric view of the device shown in FIG. 31 showing the hooks in the hair holding position.
Figure 33:
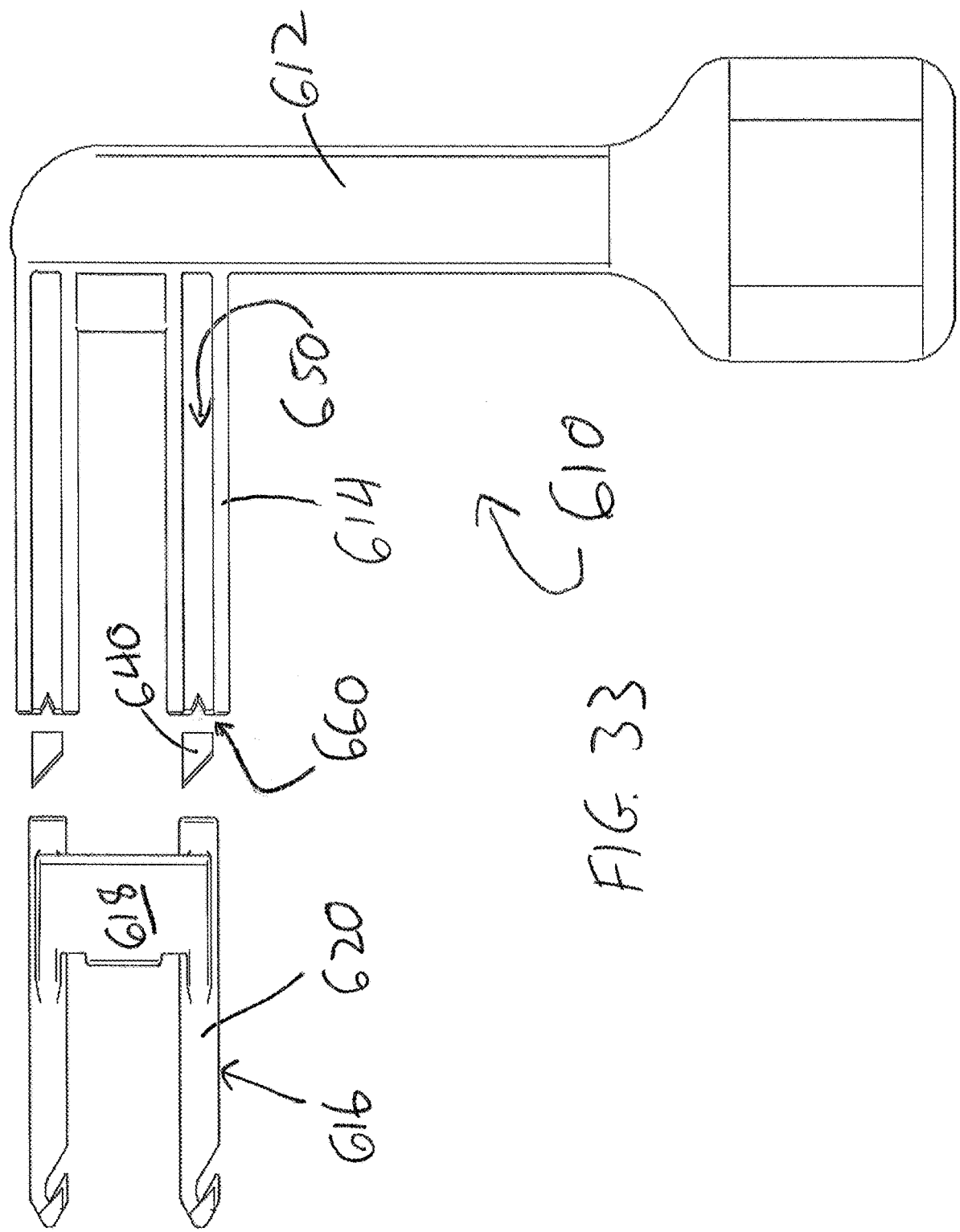
FIG. 33 is an exploded view of the embodiment shown in FIG. 31.

In the embodiment shown in FIGS. 31-33, the fingers 614 are angled relative to the handle 612. In the embodiment shown, the longitudinal axis of the fingers 614 are angled at about a ninety degree angle relative to the longitudinal axis of the handle 612. This angle could also be a 45 degree angle, or any other angle a user finds most efficient for the purpose of the device. In this embodiment, the device works in much the same way as the embodiments described above. One or more fingers 614 are combined with and may be part of the handle 612. In some embodiments, the fingers 614 may include a break away point (not shown) wherein the fingers 614 may be snapped off of the handle 612. This allows the device to be manufactured in a single size, but made smaller by removing fingers 614 if a smaller device is needed. The embodiment is shown using hooks 616 as the hair grips, however, any other of the hair grips described above may also be used. The hooks 616 are movable relative to the fingers 614 between a hair grasping position (FIG. 31) and a hair holding position (FIG. 32). The hooks 616 are similar to the hooks 16 described above and are adapted to grasp and hold an amount of hair 4. A trigger 618 is operably combined with the hooks 616 to move the hooks relative to the fingers 614. The trigger 618 may move all of the hooks 616 at the same time or in some embodiments only some or one of the hooks 616 is actuated at a time. In the embodiment shown, a single trigger 618 is combined with the base 620 of two separate hooks 616 so that the hooks 616 and trigger 618 comprise a single member, as shown in FIG. 33.

As shown in FIGS. 31 and 33, the fingers 614 include channels or openings 650 adapted to receive the base 620 portion of the hooks 616. Some embodiments further include a biasing member such as a spring (not shown) disposed between a hook 616 and the corresponding finger 614 (or handle 612) to bias the fingers 614 in their hair grasping position. After capturing an amount of hair 4 within the hook 616, the user may pull the trigger 618 back against the spring to the hair holding position to capture the hair 4 between the hooks 616 and the fingers 614 as described in more detail above.

As shown FIG. 33, some embodiments include a gap or notch 660 in the fingers 660 to help secure the hair 4 in the hair holding position. The notch 660 functions in a manner similar to the throat 26 of the hook 616 to help secure the hair 4. The notch 660 may be in a lower portion of the fingers 660, which is the portion closest to the patient's scalp when the device 610 is in use.

Some embodiments further include a detent or latch to help secure the hooks 616 in the hair holding position. The detent may be positioned between the fingers 614 and the hooks 616, between the fingers 614 and the trigger 618, or between any other combination of elements where two movable parts come into contact.

FIGS. 32 and 33 show an embodiment which includes a blade 640 for cutting excess hair during use of the device 610. The blade 640 is combined with a portion of the device 610, such as the fingers 614 or the handle 612, a predetermined distance from the hooks 616. In the embodiment shown, the blade 640 is combined within the channel 650 above the hooks 616 (i.e., closer to the use when the hooks 616 are in the hair holding position). The user may pull the trigger 618 far enough back such that hair 4 caught in the hook 616 is secured between the hook 616 and the finger 614. However, excess hair 4 extending from the hook 616 upward is cut by the blade 640 at a predetermined distance from the hook 616. In this manner an amount of hair 4 may be easily sheared off to clean the area around the laceration 8 and improve the user's view of the wound while the hair 4 below the blade remains securely retained in the hair holding position. The blade 640 may remain stationary as the hook 616 pulls the hair across the blade 640, or the blade 640 may be separately actuated to move relative to the hooks 616, for example, after the hook 616 has been moved to its hair holding position. The device may include a second detent such that the user may easily pull the trigger 618 back to the first detent to hold the hooks 616 and fingers 614 at the hair holding position but if desired pull the trigger 618 through the first detent (without cutting the hair) to a second detent (which does cut the hair) and continue to secure the components in the hair holding position. The blade 640 feature may be used with any of the other embodiments described herein.

Another feature of the invention which may be used in any of the above described embodiments includes coating a portion of the hooks and/or the finger with a substance having an increased coefficient of friction to help grab and hold the hair 4. The substance may include a rubber or ceramic based material.

The above detailed description includes references to the accompanying drawing, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A hair grasping device comprising:
   a handle;
   a first finger combined with the handle and extending from the handle in a first direction, wherein the first finger has a handle end, a grasping end, a longitudinal axis, and a width;
   a second finger combined with the handle and extending from the handle in a direction generally parallel to the first direction and spaced apart from the first finger a distance of at least the width of the first finger, wherein the second finger has a handle end, a grasping end, and a longitudinal axis;
   a first hair grip slidably combined with the first finger to be movable with respect to the first finger along the longitudinal axis of the first finger between a hair grasping position and a hair holding position of the first hair grip; and
   a second hair grip slidably combined with the second finger to be movable with respect to the second finger along the longitudinal axis of the second finger between a hair grasping position and a hair holding position of the second hair grip;
   wherein the first finger and the first hair grip are configured to secure an amount of hair therebetween when the first hair grip is moved along the longitudinal axis to the hair holding position;
   wherein the second finger and the second hair grip are configured to secure an amount of hair therebetween when the second hair grip is moved along the longitudinal axis to the hair holding position.

2. The hair grasping device of claim 1, further comprising an extrusion slidably disposed on each of the first and second fingers.

3. The hair grasping device of claim 2, further comprising a trigger operably coupled with the first hair grip and the second hair grip, and the extrusion disposed on each of the first and second fingers is operably coupled to the trigger.

4. The hair grasping device of claim 1, further comprising a trigger operably coupled with each of the first hair grip and the second hair grip.

5. The hair grasping device of claim 4, wherein each of the first hair grip and the second hair grip is disposed within a respective opening in the first finger and the second finger when in the hair holding position.

6. The hair grasping device of claim 1, wherein each of the first finger and the second finger has a notch adapted to help hold the hair.

7. The hair grasping device of claim 6, wherein each of the first and second hair grips are hooks, the hooks each having a base, a tip, and a bend.

8. The hair grasping device of claim 1, further comprising a blade disposed within each of the first and the second finger, the blade configured to cut excess haft when the first hair grip is in the hair holding position.

9. The hair grasping device of claim 1, wherein the first finger and the second finger are spaced apart such that the hair grasping device k configured to accept a finger of a second hair grasping device between the first finger and second finger.

10. A hair grasping device comprising:
    a handle;
    a first finger combined with the handle and a second finger combined with the handle, the first finger and the second finger each having a width, a handle end, a grasping end, and a longitudinal axis extending between the handle end and the grasping end, wherein the first finger is spaced from the second finger by at least the width of the first finger, and wherein the first finger extends from the handle in a direction substantially parallel with the second finger;
    a first grip having a hair engaging surface, said first grip slidably combined with the first finger to be movable with respect to the first finger along the longitudinal axis of the first finger between a hair grasping position of the first grip wherein the grasping end of the first finger is spaced apart from the hair engaging surface of the first grip and a hair holding position of the first grip wherein the grasping end of the first finger and the engaging surface of the first grip are configured to secure hair therebetween as the first grip and the first finger move longitudinally with respect to one another;
    a second grip having a hair engaging surface, said second grip slidably combined with the second finger to be movable with respect to the second finger along the longitudinal axis of the second finger between a hair grasping position of the second grip wherein the grasping end of the second finger is spaced apart from the hair engaging surface of the second grip and a hair holding position of the second grip wherein the grasping end of the second finger and the engaging surface of the second grip are configured to secure hair therebetween as the second grip and the second finger move longitudinally with respect to one another.

11. The hair grasping device of claim 10, further comprising a trigger disposed between and operably connected to the first grip and the second grip.

12. The hair grasping device of claim 11, further wherein the trigger is slidably movable with respect to the handle.

13. The hair grasping device of claim 10, wherein the first finger is configured to grasp an amount of hair and the first finger and the hair engaging surface of the first grip are coupled to securely hold the amount of hair.

* * * * *

UNITED STATES PATENT AND TRADEMARK OFFICE
CERTIFICATE OF CORRECTION

| | | |
|---|---|---|
| PATENT NO. | : 11,197,674 B2 | Page 1 of 1 |
| APPLICATION NO. | : 15/949957 | |
| DATED | : December 14, 2021 | |
| INVENTOR(S) | : David Carl Krupp et al. | |

It is certified that error appears in the above-identified patent and that said Letters Patent is hereby corrected as shown below:

In the Specification

Column 3, Line 53, replace "hair holding position" with --hair grasping position--

Signed and Sealed this
First Day of March, 2022

Drew Hirshfeld
*Performing the Functions and Duties of the
Under Secretary of Commerce for Intellectual Property and
Director of the United States Patent and Trademark Office*